United States Patent [19]
Kriesel et al.

[11] Patent Number: 5,807,323
[45] Date of Patent: Sep. 15, 1998

[54] MIXING AND DELIVERY SYRINGE ASSEMBLY

[75] Inventors: Marshall S. Kriesel, Saint Paul; Thomas N. Thompson, Richfield, both of Minn.

[73] Assignee: Science Incorporated, Bloomington, Minn.

[21] Appl. No.: 625,269

[22] Filed: Mar. 27, 1996

Related U.S. Application Data

[63] Continuation-in-part of Ser. No. 271,378, Jul. 6, 1994, Pat. No. 5,531,683, which is a continuation-in-part of Ser. No. 930,749, Aug. 13, 1992, Pat. No. 5,330,426.

[51] Int. Cl.[6] ................................................ A61M 37/00
[52] U.S. Cl. ................................................ 604/89; 604/232
[58] Field of Search .................................. 604/82, 84–89, 604/91, 200, 201, 205, 206, 412, 414, 415, 232, 234, 235

[56] References Cited

U.S. PATENT DOCUMENTS

| | | |
|---|---|---|
| 3,636,950 | 1/1972 | Gomez et al. . |
| 3,785,379 | 1/1974 | Cohen ........................................ 604/88 |
| 4,059,109 | 11/1977 | Tischlinger .............................. 604/88 |
| 4,861,335 | 8/1989 | Reynolds . |
| 5,137,511 | 8/1992 | Reynolds ................................. 604/88 |
| 5,281,198 | 1/1994 | Haber et al. . |
| 5,312,336 | 5/1994 | Haber et al. . |
| 5,360,410 | 11/1994 | Wacks . |
| 5,393,479 | 2/1995 | Haber et al. .......................... 604/87 X |
| 5,445,620 | 8/1995 | Haber et al. . |
| 5,489,267 | 2/1996 | Moreno et al. . |
| 5,569,191 | 10/1996 | Meyer ...................................... 604/88 |

Primary Examiner—Wynn Wood Coggins
Assistant Examiner—At Nguyen
Attorney, Agent, or Firm—James E. Brunton

[57] ABSTRACT

A syringe type apparatus which includes a unique fill assembly for use in controllably injecting medicinal fluids into a patient. The filling assembly includes a prefilled vial which is partially received within a novel adapter assembly that functions to operably couple the prefilled vial with the syringe assembly of the apparatus. The body of the prefilled vial is surrounded by a protective covering until immediately prior to mating the assembly with the syringe assembly.

50 Claims, 15 Drawing Sheets

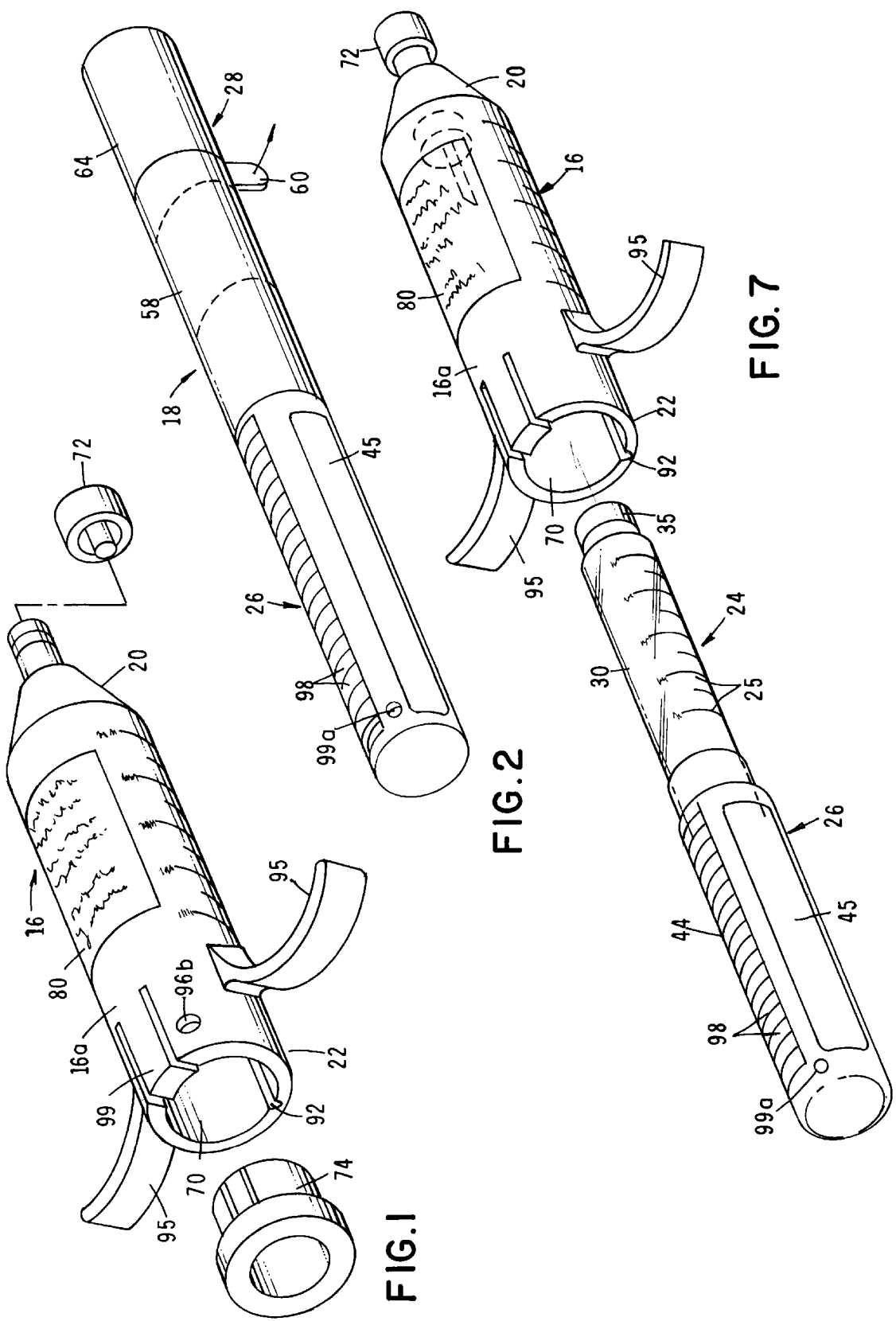

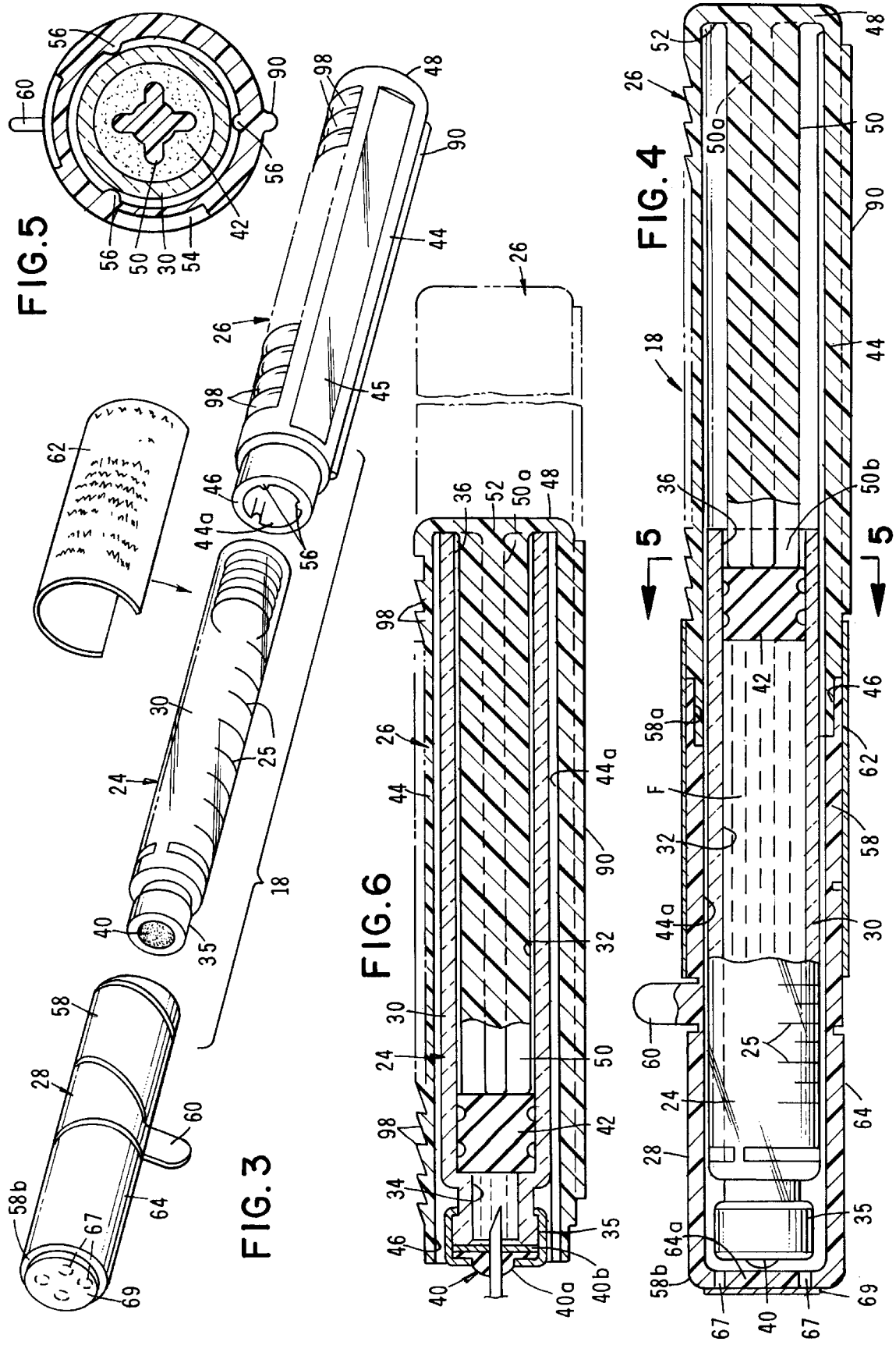

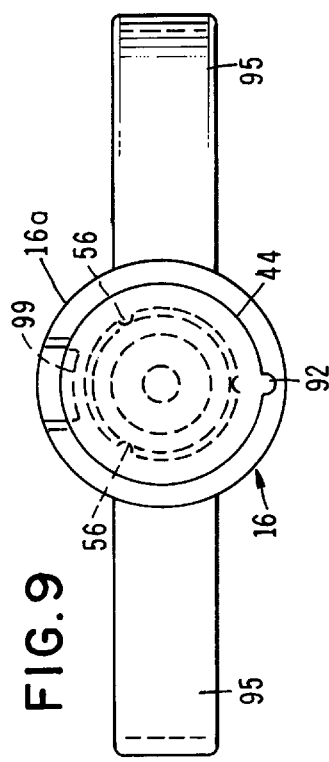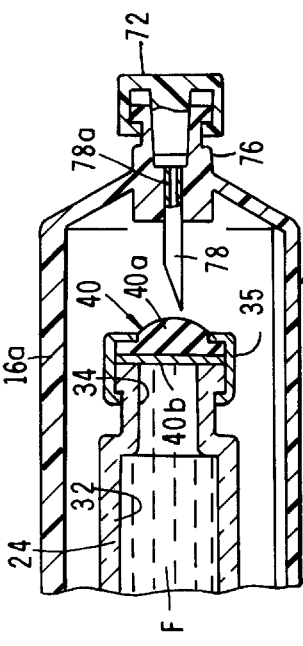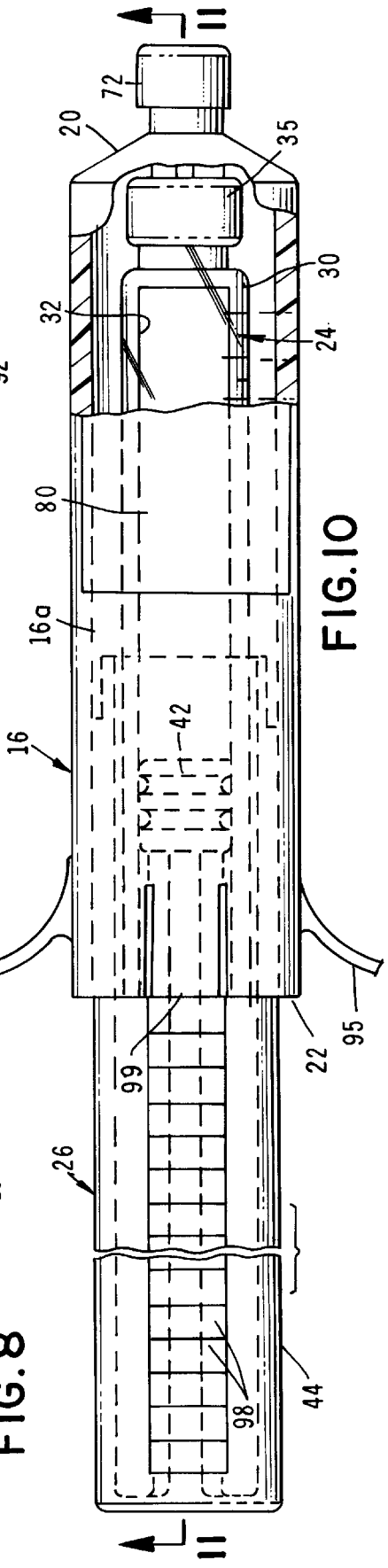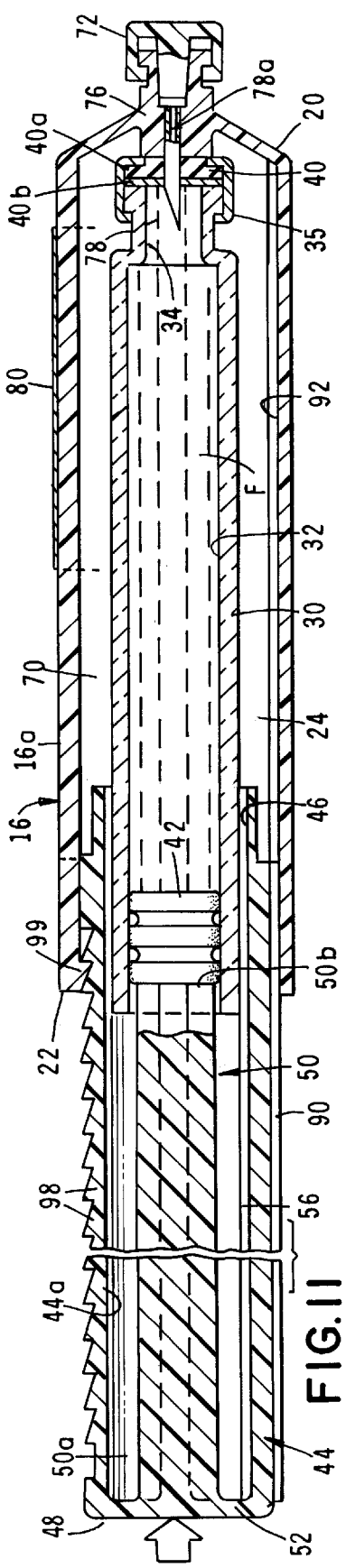

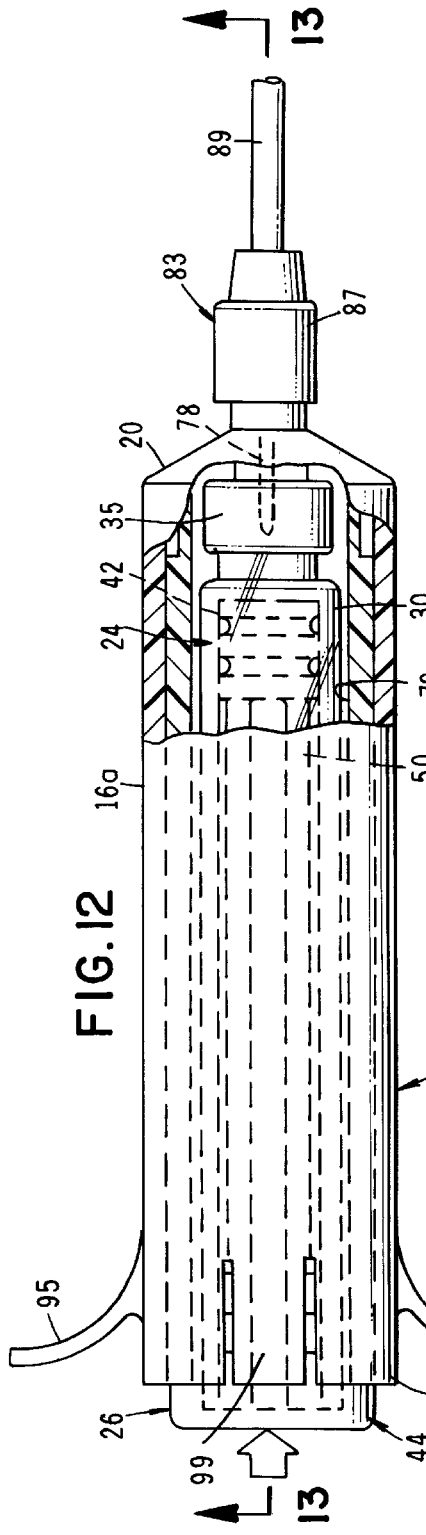
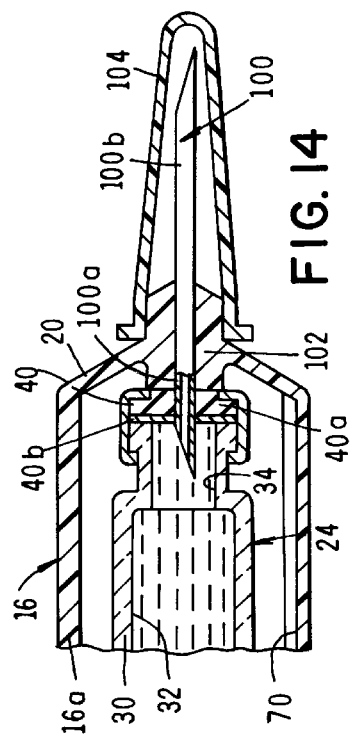
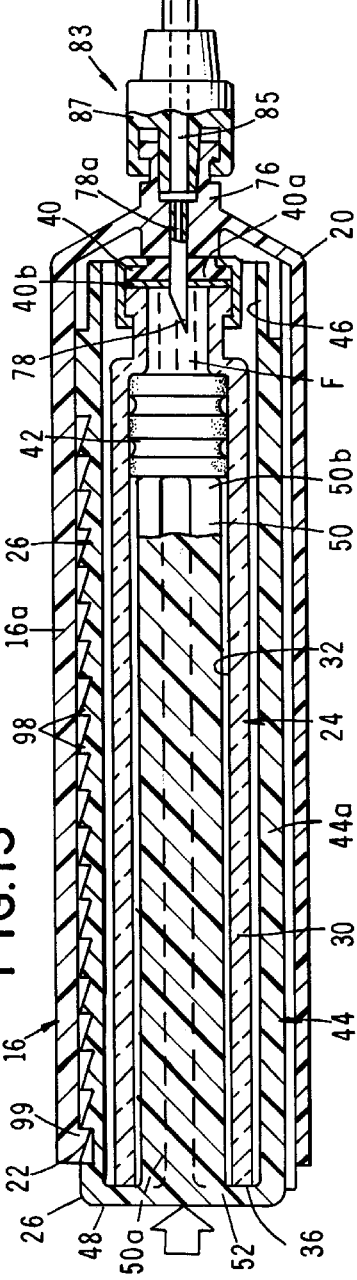

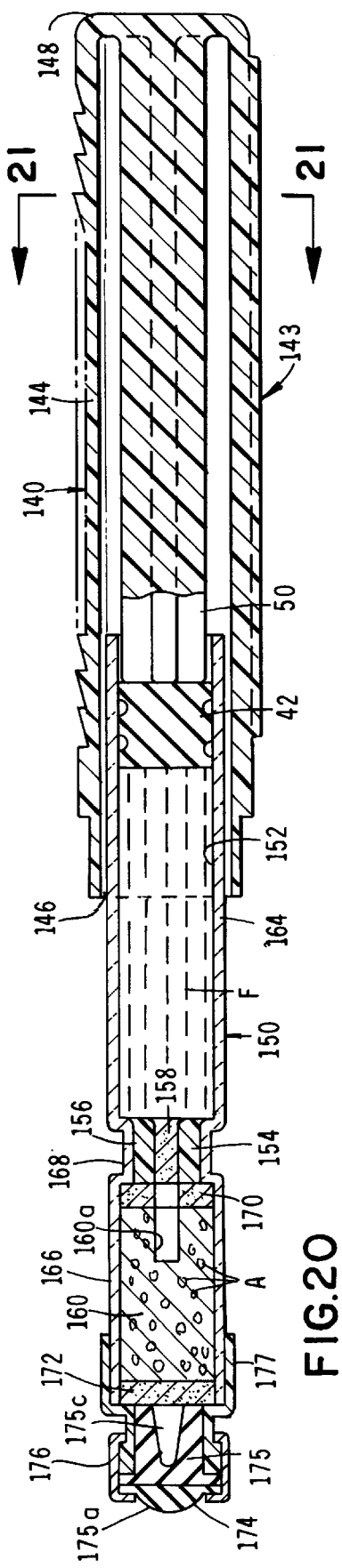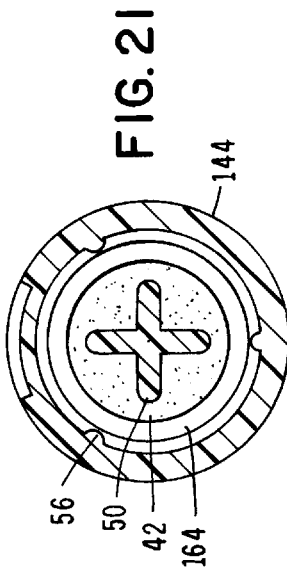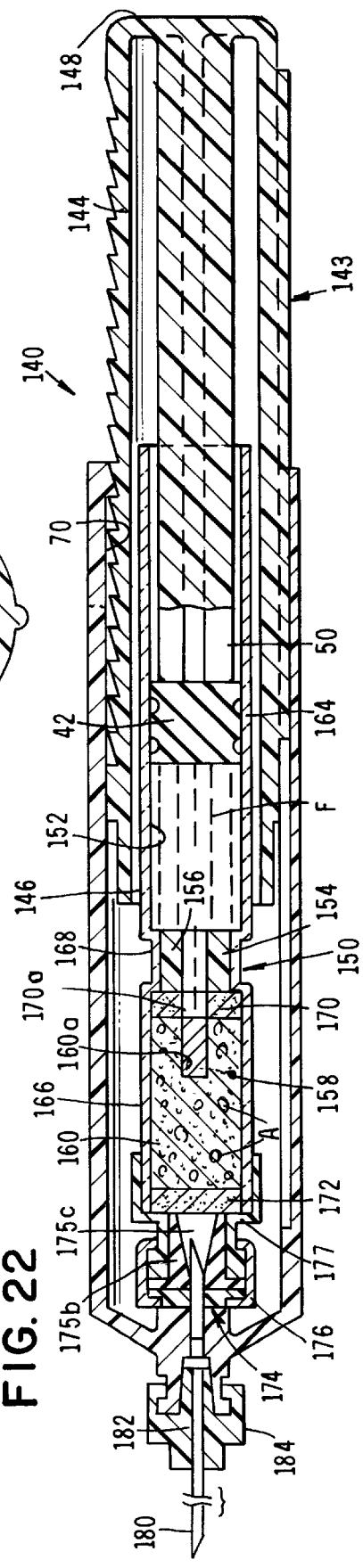

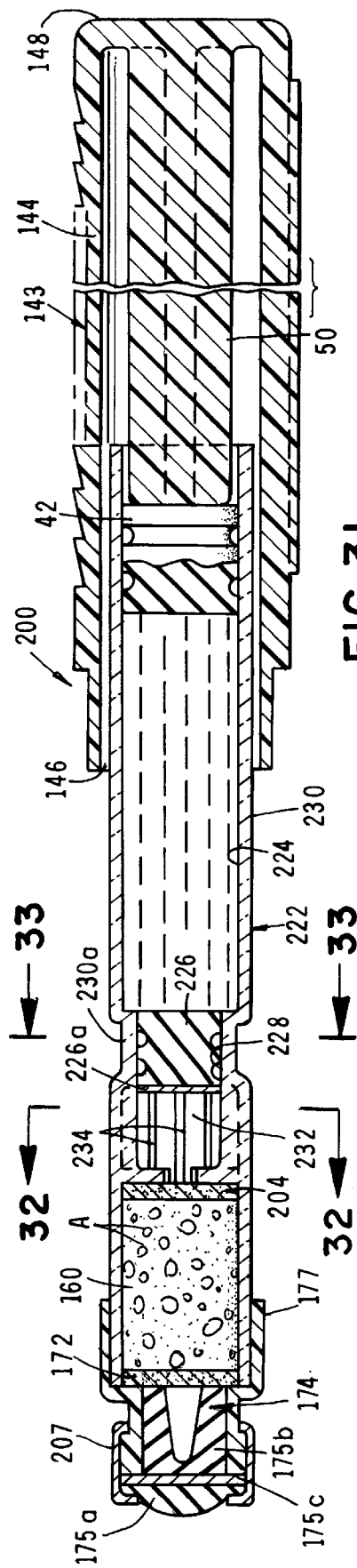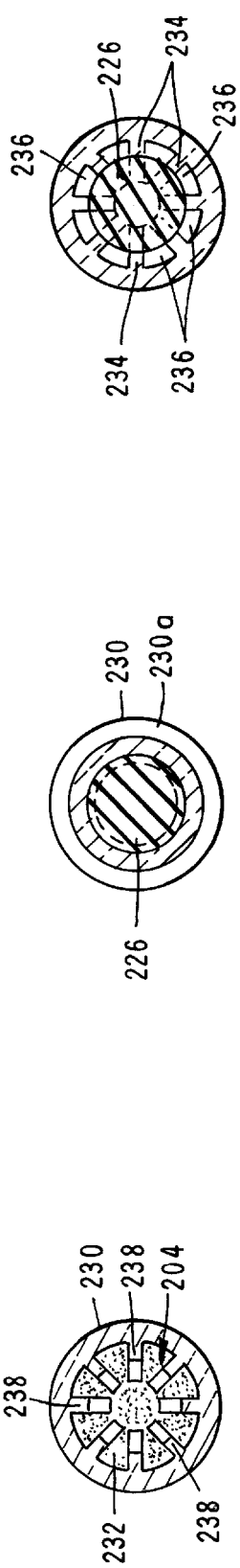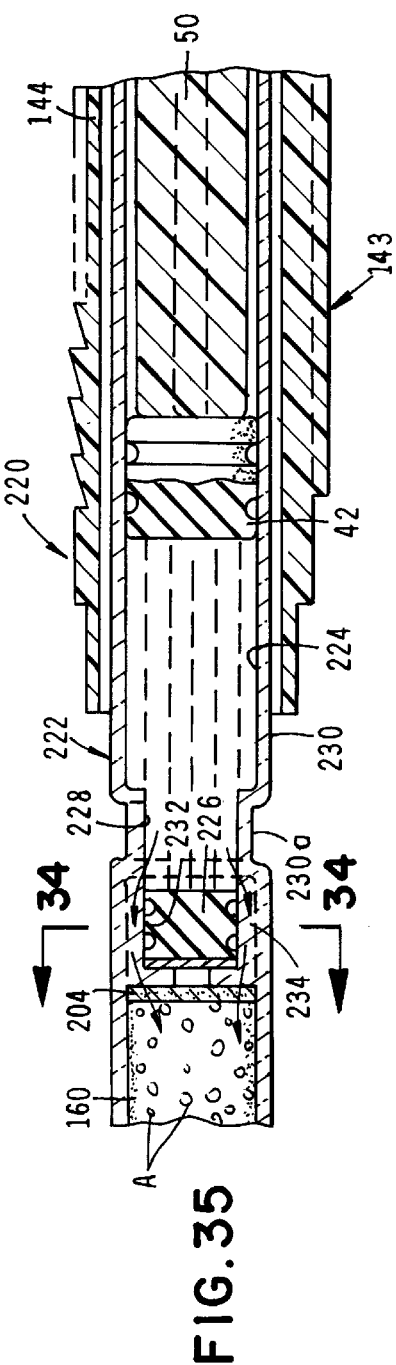

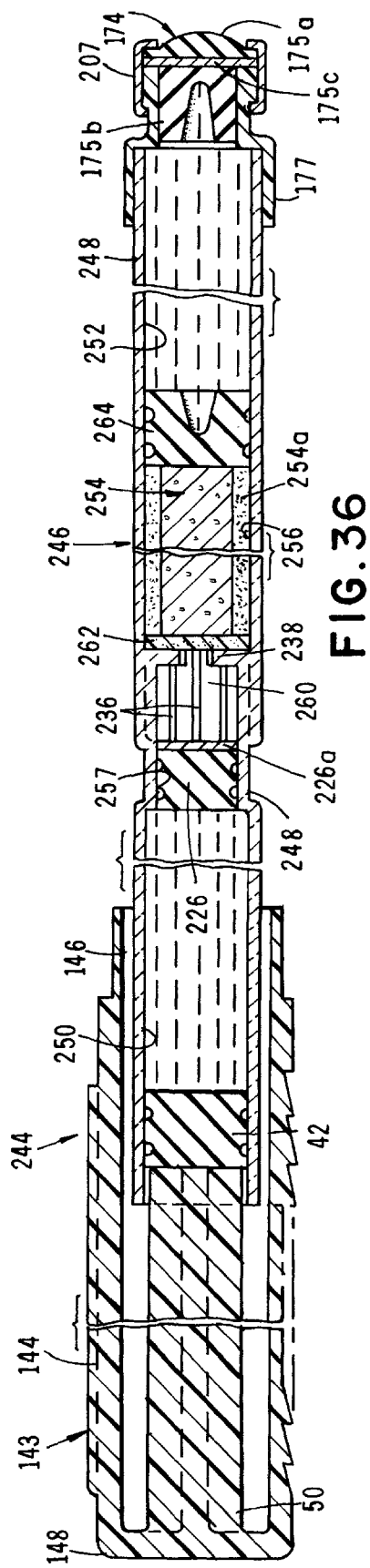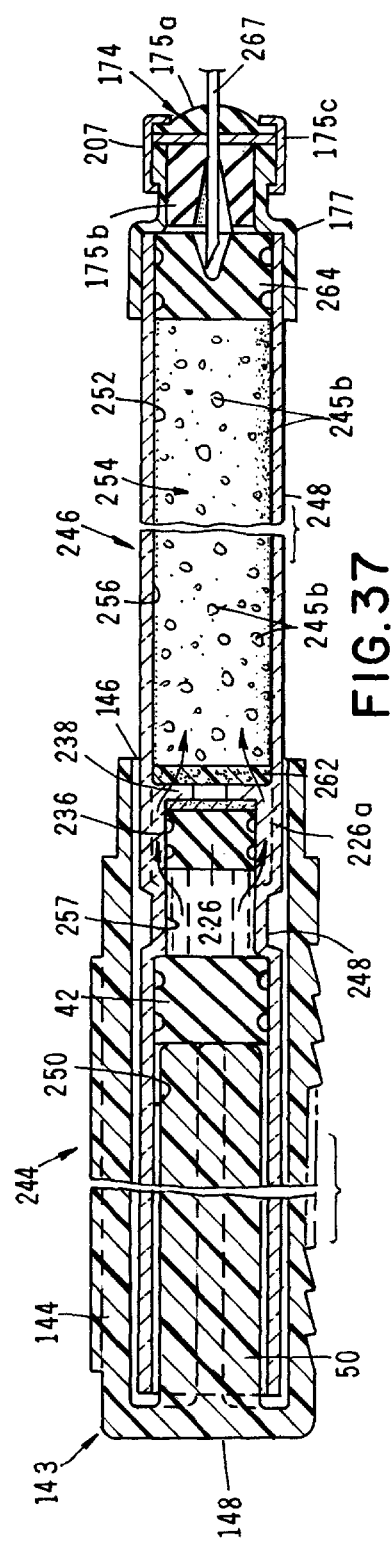

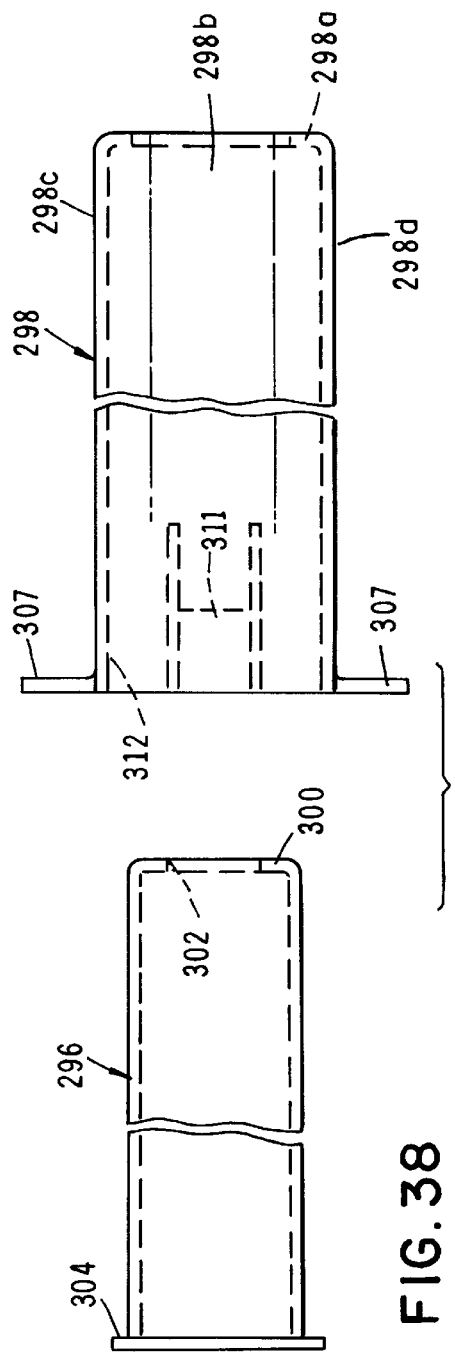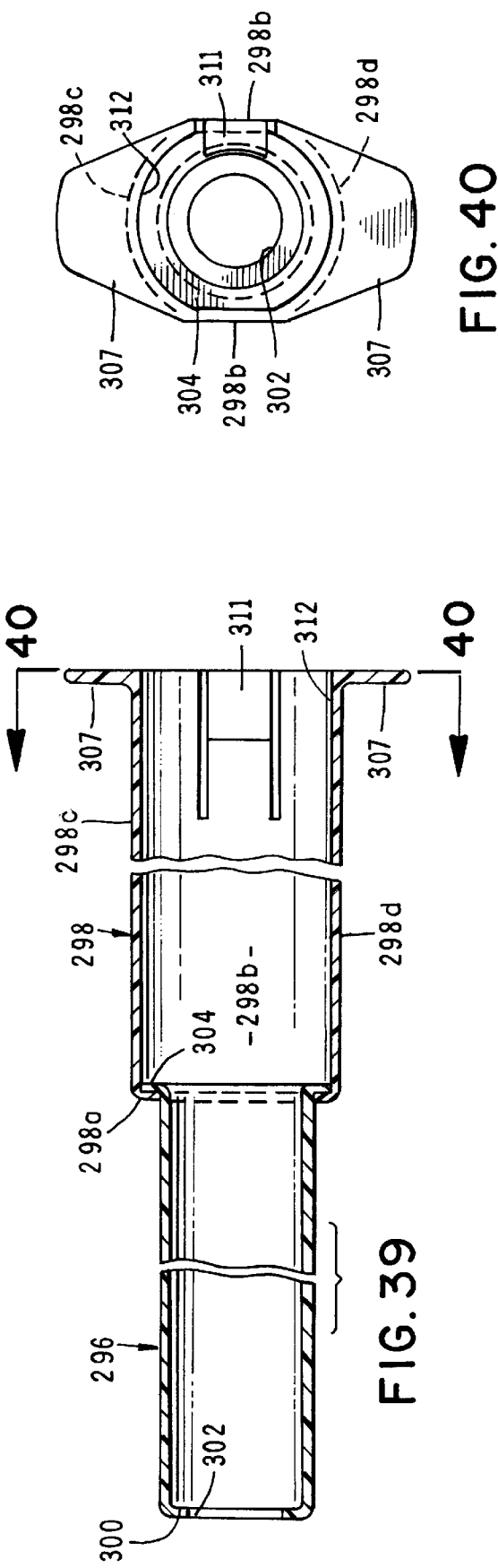

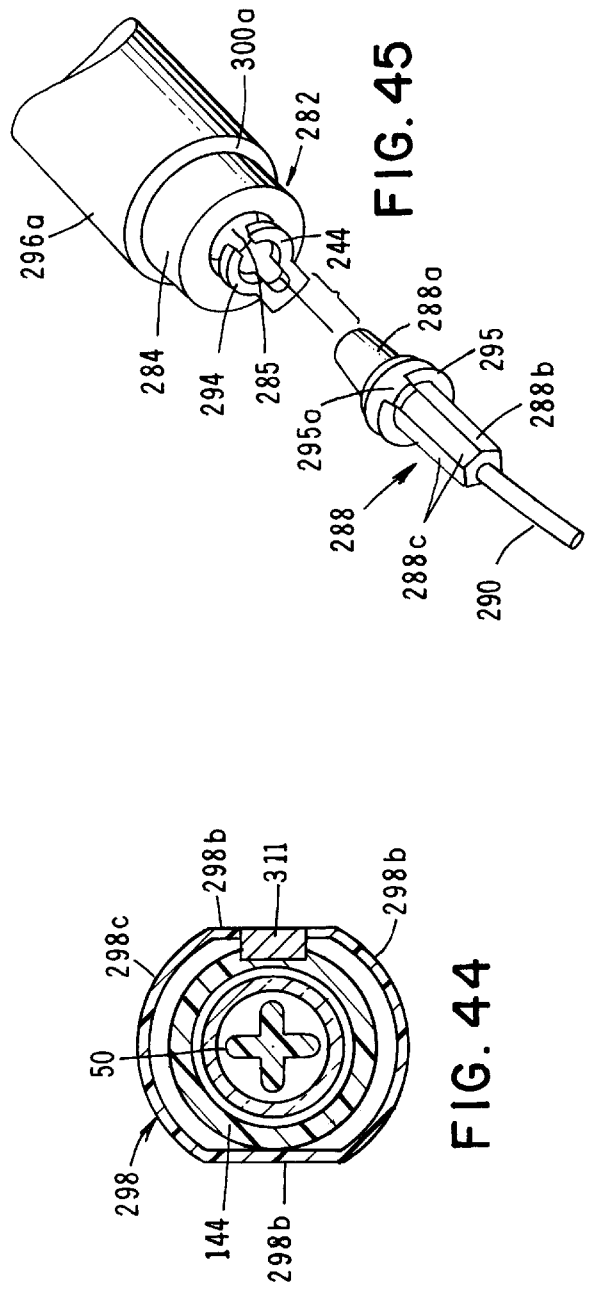
FIG. 45
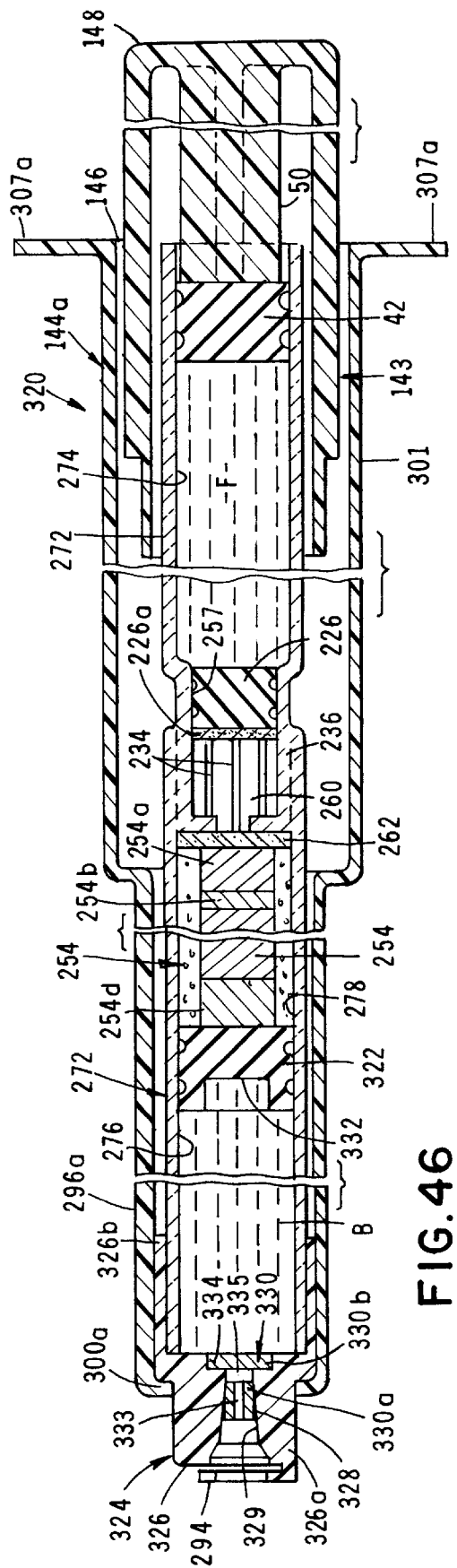
FIG. 44
FIG. 46

MIXING AND DELIVERY SYRINGE ASSEMBLY

This is a Continuation-In-Part of U.S. application, Ser. No. 08/271,378 filed Jul. 6, 1994, now U.S. Pat. No. 5,531,683, which is a Continuation-In-Part of U.S. application Ser. No. 07/930,749 filed Aug. 13, 1992, now U.S. Pat. No. 5,330,426.

BACKGROUND OF THE INVENTION

1. Field of the Invention

The present invention relates generally to syringes of the character used to administer drugs by injecting them into subcutaneous tissue. More particularly, the invention concerns a syringe of novel design in which a first component, such as a sterilized diluent, can be intermixed with a second component, such as a drug to form a beneficial agent which can be dispensed directly from the syringe.

2. Discussion of the Invention

Hypodermic syringes are commonly used for injecting into a patient beneficial agents, such as drugs in liquid form. Typically, the beneficial agent to be injected is drawn into the syringe from another container, such as a glass vial, bottle or the like having a pierceable, self-sealing stopper. When the beneficial agent, such as a pharmaceutical, is in powder form prior to injection, it must be mixed with a carrier liquid or diluent, such as saline solution, dextrose solution and sterilized water.

Mixing of powdered pharmaceuticals with the carrier liquid has been accomplished in several ways, many of them being quite crude. For example, a common practice is to inject a small quantity of the liquid carrier into the vial to dissolve the powdered component. Then, using a cannula and syringe, the solution thus formed is injected into a larger container containing the liquid carrier. This method is quite tedious and provides substantial opportunities for contamination and error.

Because in fusion of medicaments is most often accomplished in a hospital environment, it is the nurse, doctor or medical technician who mixes the drug and diluent, usually at a time shortly before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

In the past several attempts have been made to provide a syringe apparatus in which separate components can be intermixed prior to patient injection. Exemplary of such prior art devices are those disclosed in U.S. Pat. No. 2,724,383 issued to Lockhart; in U.S. Pat. No. 3,336,924 issued to Sarnoff, et al and U.S. Pat. No. 3,477,432 issued to Shaw. The Lockhart apparatus includes segregating compartments in the form of connecting, interfitting containers with associated cannula means which are manipulatable simultaneously so as to provide intercommunication between the compartments via the cannula means. The components to be mixed are stored in the interfitting containers and then are intermixed by suitably manipulating the containers. The device can be brought into "administering" condition by withdrawal of one of the empty containers to produce a hypodermic syringe type structure.

Sarnoff, et al. discloses several types of syringe packages, each comprising a vial containing a medicament, a stopper closing the vial, a connector member attached to the vial and extending beyond the stopper, and a syringe interconnected to the connector member. In one form of the Sarnoff invention, the needle of the syringes is partially embedded in the stopper. In another form of the invention, a double needle unit is carried within the connector member so that one needle can penetrate the stopper on the vial and the other can penetrate a stopper on a second container. In this last described embodiment, the double needle unit provides the flow path between the vial and the second container so that component mixing can occur.

In the Shaw patent various versions of combined mixing and injecting syringes are disclosed. The Shaw device enables intermixing of two ingredients which may be powders or liquids and provides for the injection of the mixture after the mixing step has been accomplished.

None of the prior art devices known to applicant include the unique fill assembly of the present invention which comprises a fluid containing vial assembly mounted within a unique adapter assembly which functions to conveniently mate the vial assembly with the syringe housing portion of the apparatus. Co-pending application, now U.S. Pat. No. 5,531,683 describes in detail the construction of several types of syringes. The apparatus of the present invention comprises an improvement of these devices and accordingly application, now U.S. Pat. No. 5,531,683, is hereby incorporated by reference in its entirety as though fully set forth herein. The primary improvements described in the present application relate to the provision of a unique fill assembly that can be readily mated with the syringe housing of the apparatus. In one form of the invention, the fill assembly includes adding means for adding a beneficial agent to a liquid contained within the vial portion of the fill assembly. In another form of the invention, the fill assembly includes a multi-chambered vial portion containing in one chamber a beneficial agent and in another, a novel fluid expandable means for controllably expelling the beneficial agent from the apparatus. In this latter form of the invention, the fluid expandable means can have varying volumes and swelling ratios to provide varying differential displacement vectors for patterned delivery of the beneficial agent over time.

SUMMARY OF THE INVENTION

It is an object of the present invention to provide a novel syringe apparatus for use in administering medicinal solutions by injecting the solutions intervascularly, intermuscularly, and subcutaneously. More particularly, it is an object of the invention to provide such an apparatus which includes a unique fill assembly that can be expeditiously mated with the syringe housing of the apparatus.

Another object of the present invention is to provide an apparatus of the aforementioned character in which the fill assembly comprises a vial assembly of generally conventional construction that can be prefilled with a wide variety of medicinal fluids.

Another object of the present invention is to provide a fill assembly of the type described in the preceding paragraph in which the prefilled vial assembly includes adding means and is partially received within a novel adapter assembly that functions to operably couple the vial assembly with the syringe housing of the apparatus.

Another object of the invention is to provide an adapter assembly of the type described in which the body of the prefilled vial is surrounded by a protective covering until immediately prior to mating the assembly with the syringe housing.

Another object of the invention is to provide an apparatus as described in the preceding paragraphs in which the adapter assembly includes locking means for locking the assembly to the syringe housing following mating of the adapter assembly therewith.

Another object of the invention is to provide an apparatus of the class described in which the fill assembly includes adding means for adding a beneficial agent to a liquid component contained within the fill assembly.

Another object of the invention is to provide an apparatus in which the fill assembly includes a multi-chamber container having a beneficial agent in one chamber and a novel fluid expandable material in another chamber for controllably expelling the beneficial agent over time in accordance with various medicinal protocols.

Another object of the invention is to provide a novel adapter assembly for use with the syringe housing which is easy to use, is inexpensive to manufacture, and one which maintains the prefilled vial in an aseptic condition until time of use.

Other objects of the invention are set forth in Ser. No. 07/930,749 which is incorporated herein by reference and in Ser. No. 08/271,378 which is incorporated by reference.

BRIEF DESCRIPTION OF THE DRAWINGS

FIG. 1 is a generally perspective, exploded view of one form of the syringe assembly of the present invention.

FIG. 2 is a generally perspective view of one form of the fill assembly of the apparatus.

FIG. 3 is a generally perspective, exploded view of one form of the fill assembly of the present invention.

FIG. 4 is an enlarged, cross-sectional view of the fill assembly illustrated in FIG. 3 as it appears in the assembled configuration.

FIG. 5 is an enlarged, cross-sectional view taken along lines 5—5 of FIG. 4.

FIG. 6 is a cross-sectional view similar to FIG. 4, but showing the appearance of the component parts of the fill assembly after the plunger of the container has been telescopically moved from a first to a second position.

FIG. 7 is a generally perspective, exploded view of the apparatus of the invention showing the syringe assembly and fill assembly as they appear prior to mating the fill assembly with the syringe assembly.

FIG. 8 is a fragmentary, cross-sectional view of the right-end portion of the apparatus as the component parts appear immediately prior to final mating of the fill assembly with the syringe assembly.

FIG. 9 is a left-end view of the syringe housing of the syringe assembly of the invention.

FIG. 10 is an enlarged, side elevational view of the apparatus showing the fill assembly mated with the syringe housing and being partly broken away to show internal construction.

FIG. 11 is a cross-sectional view taken along lines 11—11 of FIG. 10.

FIG. 12 is a side-elevational view, partly in cross section, of the fully assembled apparatus shown in FIG. 11 showing the appearance of the component parts thereof after the plunger of the fill assembly has been moved into its fully forward position.

FIG. 13 is a cross-sectional view taken along lines 13—13 of FIG. 12.

FIG. 14 is a fragmentary, cross-sectional view of the forward portion of another form of the apparatus of the present invention.

FIG. 20 is an enlarged, cross-sectional view of an alternate form of the container and adapter subassemblies of the fill assembly of the invention.

FIG. 21 is a cross-sectional view taken along lines 21—21 of FIG. 20.

FIG. 22 is an enlarged, cross-sectional view of the form of the apparatus shown in FIG. 20 after it has been operably coupled with the syringe assembly of the invention.

FIG. 31 is a cross-sectional view of still another form of the container and adapter subassemblies of the fill assembly of the invention.

FIG. 32 is a cross-sectional view taken along lines 32—32 of FIG. 31.

FIG. 33 is a cross-sectional view taken along lines 33—33 of FIG. 31.

FIG. 34 is a cross-sectional view taken along lines 34—34 of FIG. 35.

FIG. 35 is a fragmentary, cross-sectional view of the forward portion of the apparatus shown in FIG. 31 showing advancement of the plunger during the fluid delivery step.

FIG. 36 is a cross-sectional view of yet another form of the container and adapter subassemblies of the fill assembly of the invention.

FIG. 37 is a fragmentary, cross-sectional view of the forward portion of the apparatus shown in FIG. 31 illustrating the position of the various component parts of the device at the completion of the fluid delivery step.

FIG. 38 is a side-elevational, cross-sectional view of an alternate form of the syringe assembly of the present invention.

FIG. 39 is a side-elevational, cross-sectional view of the alternate form of the syringe assembly shown in FIG. 38, but showing the component parts thereof in an assembled configuration.

FIG. 40 is a view taken along lines 40—40 of FIG. 39.

FIG. 44 is a cross-sectional view taken along lines 44—44 of FIG. 43.

FIG. 45 is a generally perspective fragmentary view of the forward portion of the apparatus of this latest form of the invention illustrating a portion of the fluid delivery subassembly of the device in position to be mated with the fill assembly.

FIG. 46 is a side-elevational, cross-sectional view of still another form of the container and adapter subassemblies of the fill assembly of the invention mated with the alternate form of syringe assembly shown in FIGS. 38 and 39.

DESCRIPTION OF ONE FORM OF THE INVENTION

Figure 15:
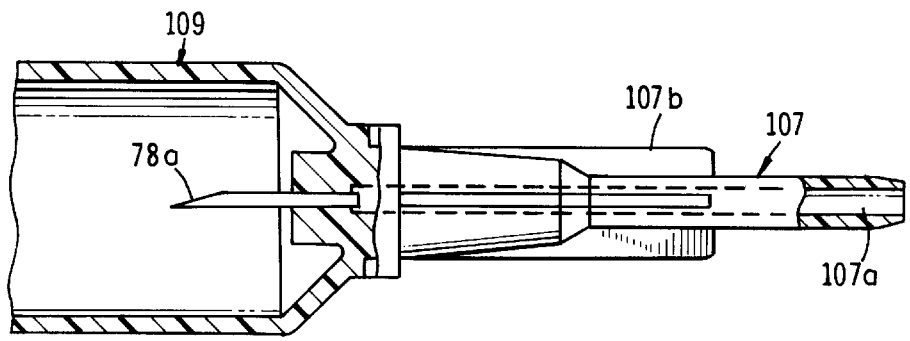
FIG. 15 is a fragmentary, cross-sectional view of the forward portion of another embodiment of the invention having a blunt end cannula instead of a conventional needle-type cannula.

Referring to the drawings and particularly to FIGS. 1 through 3, one form of the apparatus of the present invention is there illustrated. The apparatus here comprises two main assemblies, namely a syringe assembly 16 (FIG. 1) and a fill assembly 18 (FIG. 2) which can be operably mated with the syringe assembly in a manner presently to be described. Syringe assembly 16, the details of construction of which will presently be described, is similar in some respects to the syringe assembly described in Ser. No. 08/271,378, now U.S. Pat. No. 5,531,683, and includes a hollow housing 16a having first and second ends 20 and 22.

As best seen by referring to FIGS. 2, 3, and 4, the fill assembly portion 18 of the apparatus comprises a container subassembly 24, an adapter subassembly 26, and a cover subassembly 28, the character of which will presently be described. Container subassembly 24 includes a body portion 30, having a fluid chamber 32 for containing an injectable fluid "F" (FIG. 4). Chamber 32 is provided with first and second open ends 34 and 36 (FIGS. 4 and 6). First open end 34 is sealably closed by closure means here provided in the form of a pierceable septum assembly 40. Septum assembly 40 includes a pierceable septum 40a and a permeability barrier disc 40b affixed to septum 40a and is held securely in position by a clamping ring 35. As best seen in FIGS. 4 and 6, a plunger 42 is telescopically movable within chamber 32 of container subassembly 24 from a first location shown in FIG. 4 where it is proximate open end 36 to a second position shown in FIG. 6 where it is proximate open end 34. The vial portion of the container subassembly 24 can be constructed of various materials such as glass and plastic.

Referring particularly to FIGS. 3 and 4, it can be seen that the adapter subassembly 26 comprises a hollow housing 44 having a first open end 46 and a second closed end 48 (FIG. 6). Container subassembly 24 is telescopically receivable within open end 46 of housing 44 in the manner shown in FIG. 4 so that the housing can be moved from the first extended position shown in FIG. 4 to the vial encapsulation position shown in FIG. 6. Forming an important part of the adapter subassembly is pusher means shown here as an elongated pusher rod 50 which functions to move plunger 42 within fluid chamber 32 from the first position shown in FIG. 4 to the second position shown in FIG. 6. In the form of the invention shown in the drawings, pusher rod 50 has a first end 50a interconnected with a closure wall 52 of housing 44 and an opposite end 50b which engages plunger 42 and causes telescopic movement of the plunger within chamber 32 of container subassembly 24 as housing 44 is moved from the extended position into the vial encapsulating position shown in FIG. 6.

As best seen by referring to FIGS. 3 and 5, the interior wall 44a of housing 44 is provided with circumferentially spaced-apart protuberances 56 which engage and center container subassembly 24 within housing 44. Due to the small surface area presented by protuberances 56, there is little frictional resistance to the sliding movement of container subassembly 24 relative to housing 44 as the housing is moved from the extended position shown in FIG. 4 into the vial encapsulating position shown in FIG. 6.

Referring to FIG. 3, it is to be noted that cover subassembly 28 of the fill assembly of the present form of the invention includes a spiral wound, frangible portion 58 having a first open end 58a for telescopically receiving body portion 30 of container subassembly 24 (FIG. 4) and a second closed end 58b. Portion 58 initially circumscribes a major portion of container subassembly 24 in the manner best seen in FIG. 4. An integral pull tab 60 is provided to permit the spiral wound, frangible portion to be pulled from container subassembly 24 so as to expose a substantial portion of body 30. As best seen in FIGS. 3 and 4, a medicament label 62 circumscribes spiral wound portion 58 and serves to join parts 44 and 64 and prevents unintended unwinding of the spiral portion from the container subassembly 24. However, upon pulling tab 60, the spiral portion will unwind and, in so doing, will tear medicament label 62 so that the spiral portion 58 of the covering as well as the cylindrical portion 64 which, also comprises a part of the cover assembly, can be slipped from the container 24 so as to expose to view septum assembly 40. Septum assembly 40 includes a pierceable septum body 40a and a pierceable interfacial barrier member 40b.

As shown in FIGS. 3 and 4, apertured end 64a of cylindrical portion 64 of subassembly 28 is provided with venting apertures 67 which are covered by a porous vent patch 69 which can be constructed from any suitable porous material, such as a material sold by DuPont under the name and style "TYVECH", that will permit air entrapped within the interior of cover subassembly 28 to be expelled to atmosphere as the subassembly is placed over container subassembly 24.

Turning to FIGS. 1 and 9 through 13, the syringe assembly 16 of the apparatus of the invention can be seen to include the previously mentioned hollow housing 16a which defines an internal chamber 70.

The first end 20 of housing 16a is temporarily closed by a removable cap 72, while the second end 22 is closed by a removable closure plug 74. Connected to an end wall 76 is cannula means for providing a fluid flow path from housing 16a. The cannula means here comprises a hollow piercing cannula 78 having an internal flow passageway 78a which can be placed in communication with chamber 32 of container 24 in a manner presently to be described (FIG. 8).

In using the apparatus of the invention, with the fill assembly in the filled configuration shown in FIG. 4, the cover subassembly is first removed from the container subassembly by pulling on pull-tab 60. This will cause the spiral portion 58 of the cover subassembly to tear away from the container subassembly so that it can be separated from the forwardly disposed portion 64. Once the spiral wound portion 58 is removed, cylindrical portion 64 can also be removed and discarded. Removal of the cover subassembly exposes the forward portion of the container subassembly and readies the fluid containing assembly, which includes the container subassembly and the adapter subassembly, for interconnection with the syringe assembly 16.

Mating of the adapter subassembly with the syringe assembly is accomplished by first removing plug 74 and then telescopically inserting the exposed container portion of the container subassembly 24 of the fluid containing assembly into chamber 70 and pushing the fluid containing assembly forwardly of housing 16a. As the adapter subassembly approaches a seated position within chamber 70 (FIG. 8), the piercing cannula 78 connected to wall 76 will pierce septum assembly 40 of the container subassembly opening a fluid flow path between the hollow cannula and the fluid reservoir or chamber 32 of container 24.

Following removal of cap 72, and the sealable interconnection with housing 16a of a fluid delivery administration line assembly 83 (FIGS. 12 and 13), a continued inward movement of the adapter subassembly will cause pusher rod 50 thereof to move plunger 42 forwardly of chamber 32 to a position shown in FIGS. 12 and 13. As plunger 42 is moved forwardly of chamber 32, fluid contained within the chamber will flow through the hollow cannula into passageway 85 of a connector 87 which forms a part of the fluid delivery administration line assembly 83. Assembly 83, as well as luer connector 87 are of conventional construction well known to those skilled in the art. As fluid under pressure flows into passageway 85, it will enter an administration line 89 and will flow outwardly of the device in the manner shown by the arrow "A" in FIG. 13. Adapter subassembly housing 44 is provided with a longitudinally extending protuberance 90 (FIG. 3) which is receivable within a polarization groove 92 formed in syringe body 18 (FIG. 9) so that housing 44 can be received within the syringe body in a proper orientation to enable proper irremovable locking of the adapter subassembly with the syringe housing. Adapter housing 44 also has a viewing window 45 through which spaced apart indicia 25 provided on container 24 can be viewed during the fluid dispensing step.

Syringe housing 16a is provided with outwardly extending finger engaging elements 95 which can be engaged by the fingers of the user during the telescopic insertion of the fill assembly into the syringe body. Circumscribing housing 16a is a medicament and use label 80 (FIG. 1).

Materials suitable for use in constructing syringe housing 16a and adapter assembly housing 44 include metals and plastics, preferably polyethylene, polypropylene, polyvinyl chloride, and nylon. Materials suitable for constructing container 24 include glass and various plastics that are compatible with the liquids they contact and are preferably non-permeable type materials. Container body 30 may also be provided with various internal coatings, such as silicone for use as plunger slip agents and for purposes of biocompatability.

In order to securely lock the adapter subassembly with the syringe assembly after mating thereof has been accomplished locking means are provided. The locking means here comprise a series of locking teeth 98 which are constructed so that they will slide under a flexible locking tab 99, which is provided proximate the entrance of chamber 70 of syringe housing 16a, as the adapter subassembly is urged inwardly of chamber 70 (FIG. 11). However, once the adapter subassembly has reached the fully forward position shown in FIG. 13, locking tab 99 will engage one of the teeth and effectively prevent removal of housing 44 of the adapter subassembly from chamber 70. With this novel construction, once the adapter assembly is mated with the syringe housing, it cannot be removed therefrom thereby preventing system misuse or adulteration. Referring to FIGS. 1 and 2, it is to be observed that when the adapter assembly is fully forward, an indicating indicia such as a dot 99a provided on the adapter housing is viewable through an aperture 99b which is strategically located on the syringe body to indicate full excursion of the adapter assembly into the syringe housing.

Turning to FIG. 14 another form of the apparatus of the invention is there shown. This apparatus is similar in construction and operation to that shown in FIGS. 1 through 13 save that a double ended piercing cannula 100 is mounted in end wall 102 of the syringe body. Cannula 100, which includes an inboard portion 100a and an outboard portion 100b is of a construction that is well known to those skilled in the art and enables one end 100a of the cannula to be used to pierce the septum of the container assembly and end 100b to pierce the septum of a medicament vial for mixing as described in Ser. No. 08/271,378. End 100b can also be used to pierce the skin of the patient so as to permit injection of the fluid "F". Prior to use, the outwardly projecting portion 100b of cannula 100 is covered by a plastic cover cap 104.

Referring next to FIG. 15, still another alternate end construction is there shown. The apparatus shown in FIG. 15 is similar in construction and operation to that previously described herein, save that needle 100 has been replaced with a blunt end cannula 107 of the character adapted to penetrate a slit septum, as for example, a slit septum provided in the inlet port of a fluid delivery device used for dispensing medicinal fluids. Exemplary of such fluid delivery devices are those described in U.S. Pat. No. 5,279,558, which has a pierceable septum sealably mounted within the inlet port of the device (see, for example, FIG. 66). Because of the pertinence of U.S. Pat. No. 5,279,558, this patent, which was issued to one of the present inventors, is hereby incorporated herein by reference as though fully set forth herein. Blunt end cannula 107 is of conventional construction and includes a central fluid passageway 107a which communicates with the fluid passageway of a hollow cannula 78a which extends into the interior of a syringe body 109 of the character previously described. Cannula 107 can be integrally formed with the syringe body, or as shown in FIG. 15, can be removably interconnected therewith. Wings 107b are provided to assist in twisting the cannula assembly in interconnecting it with the syringe body. Such a cannula construction is also well known in the art.

Figure 16:
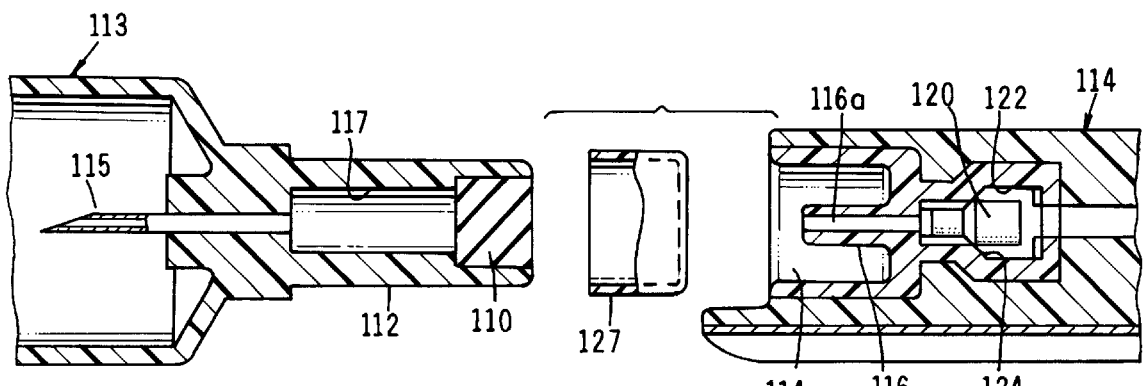
FIG. 16 is a fragmentary, cross-sectional, exploded view of the forward portion of yet another form of syringe assembly of the invention along with a closure cap and a portion of a fluid delivery device with which the syringe assembly can be used.

Referring next to FIG. 16, still another alternate form of the apparatus of the invention is there shown. This apparatus is also similar in construction to the earlier described embodiments. However, this latest form of the invention is adapted to be used with a dispensing device 114 of the character having an inlet port 114a of the general configuration shown in FIG. 16. More particularly, the dispensing device, which is generally designated in FIG. 16 as 114, includes a blunt cannula 116 which extends into inlet port 114a so that when cylindrical extension 112 of the syringe assembly is telescopically received therewithin the blunt cannula 116 will penetrate an elastomeric slit septum 110 carried within a cylindrical extension 112 provided on a syringe housing 113, which is of the general character previously described. Upon penetration of the slit septum, fluid will be free to flow from the syringe assembly through a passageway 115a provided in cannula 115 into a chamber 117 and then into passageway 116a of the blunt cannula and in a direction toward a valve means provided with the inlet portion of the dispensing device. This valve means here comprises a valve member 120 which is movable within a chamber 122 between the valve closed portion shown in FIG. 16, wherein the valve member is seated against a valve seat 124, to a valve open position wherein the valve member is moved away from the valve seat due to the urging of the fluid flowing under pressure toward chamber 122. Dispensing device 114 is also of similar construction to those disclosed in U.S. Pat. No. 5,279,558.

Figure 17:
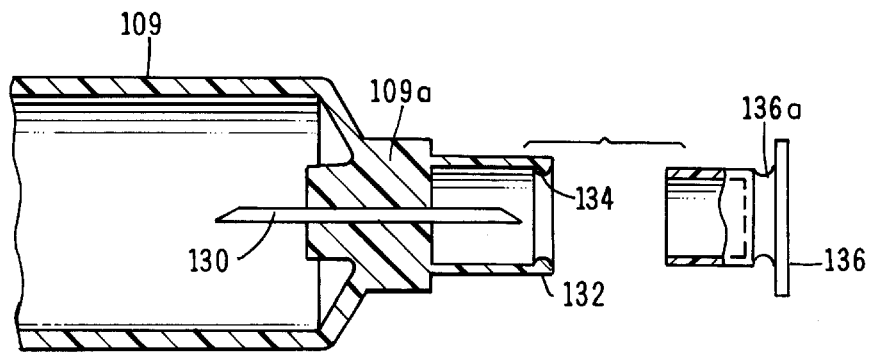
FIG. 17 is a fragmentary, cross-sectional, exploded view of the forward portion of still another form of the invention.

In this latest construction, a closure cap 127 is sealably receivable over the outboard end of cylindrical extension 112. Closure cap 127 seals the outlet port of the syringe assembly and protects the slit cannula from damage and contamination Turning to FIG. 17, still another embodiment of the invention is there shown. This embodiment is also similar in construction and operation to that shown in FIG. 14 save that a double ended piercing cannula 130 extends only a limited distance outwardly from the end wall 109a of syringe housing 109. Further, a generally cylindrical extension 132 is provided on the syringe body which circumscribes the cannula and prevents needle stick as well as protecting the needle from contamination. In this latest construction, extension 132 includes a circumferentially extending bead 134 which mates with a channel 136a provided in a closure cap 136. With this construction, closure cap 136 snaps into locking engagement with extension 132 when the cap is telescopically inserted into extension 132 and seated with respect thereto. The apparatus shown in FIG. 17 is also usable with dispensing devices of the general character discussed in U.S. Pat. No. 5,279,558.

Figure 18:
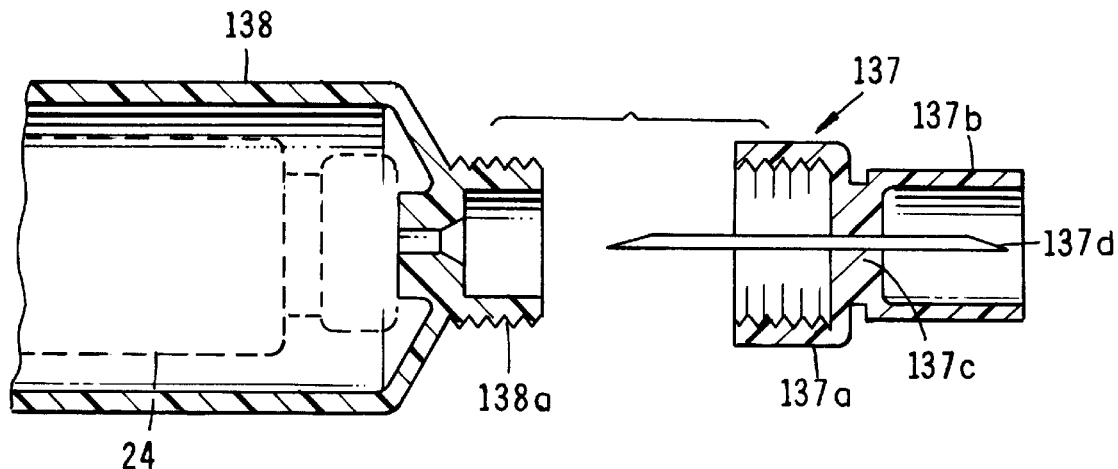
FIG. 18 is a fragmentary, cross-sectional, exploded view of the forward end portion of another form of the syringe assembly of the invention along with a coupling assembly.

Turning to FIG. 18, yet another embodiment of the invention is there shown. This apparatus includes a coupling assembly 137 and a syringe assembly 138 which is similar in construction to those previously described herein. Coupling assembly 137 is specially designed to operably couple together the syringe assembly 138 and a fluid dispenser of the general character described in U.S. Pat. No. 5,279,558, which patent has been incorporated herein by reference.

Figure 19:
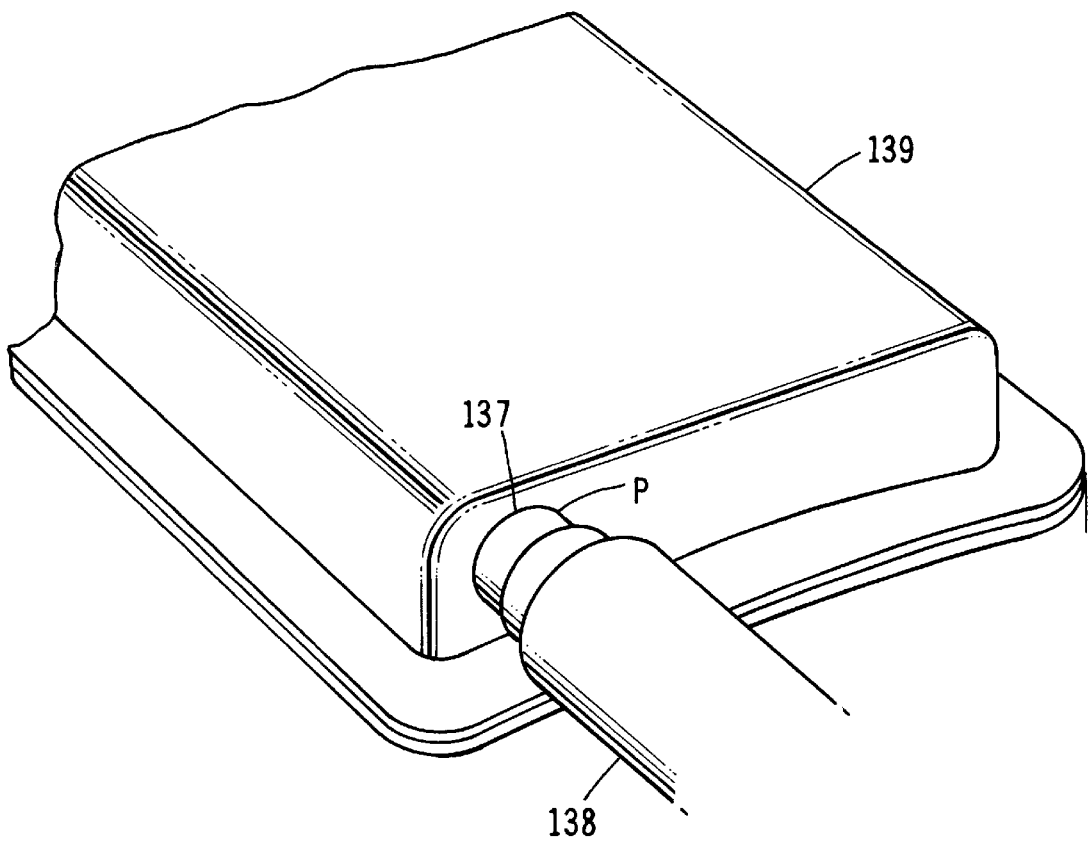
FIG. 19 is a generally perspective, fragmentary view showing the syringe assembly of FIG. 18 mated with a fluid dispensing device.

In this latest embodiment of the invention, a threaded cylindrical extension 137a of coupling 137 is threadably receivable over a mating threaded cylindrical extension 138a provided on syringe assembly 138. An oppositely disposed cylindrical extension 137b provided on coupling assembly 137 is adapted to mate with an inlet port "P" provided on a fluid dispenser 139 (FIG. 19). Fluid dispenser 139 is of the same general character as the fluid dispensers described in U.S. Pat. No. 5,279,558 and includes a base and a distendable membrane which cooperates with the base to form a fluid chamber.

A central partition 137c of coupling assembly 137 separates the cylindrical extensions 137a and 137b and functions to support a hollow cannula 137d. Cannula 137d may be a conventional piercing, needle type cannula or it may be a blunt end cannula. When coupling assembly 137 is mated with the syringe assembly, the inboard end of cannula 137d will function to pierce the septum of the container subassembly 24 while the other outboard end of the cannula will function to pierce a septum mounted within the inlet port of the fluid dispenser 139 (not shown in FIG. 19).

Referring next to FIGS. 20 through 23, another form of adapter and container subassembly of the invention is there shown and generally designated by the numeral 140. The subassemblies are similar in many respects to those shown in FIGS. 3 and 4 and like number are used to identify like components. The adapter subassembly 143 here comprises a hollow housing 144 having a first open end 146 and a second closed end 148 (FIG. 20). Container subassembly 150 is telescopically receivable within open end 146 of housing 144 in the manner shown in FIG. 20 so that the housing can be moved from the first extended position shown in FIG. 20 toward the advanced position shown in FIG. 22. As before, the adapter subassembly includes pusher means shown here as an elongated pusher rod 50 (see also FIG. 21) which functions to first move plunger 42 within fluid chamber 152 from the first position shown in FIG. 20 to the second position shown in FIG. 22 and, then finally into a fully inserted position wherein the plunger seats against a flow control means shown here as a hollow plug assembly 154. Plug assembly 154 here comprises an annular shaped plug 156 and a generally cylindrically shaped stopper plug 158 which is movable by fluid pressure from the fluid flow blocking position shown in FIG. 20 to the fluid flow open position shown in FIG. 22.

A unique feature of the container subassembly 140 of this latest form of the invention is the provision of adding means, which is here shown as a scaffold 160 having an additive "A" removably affixed thereto. The nature of the adding means as well as the various beneficial agents which can comprise additive "A" are discussed in detail in U.S. Ser. No. 08/271,378, now U.S. Pat. No. 5,531,683, which is incorporated herein by reference.

As best seen in FIG. 20, fluid chamber 152 is defined by a generally cylindrically shaped, rearward container portion 164 while a generally cylindrically shaped forward container portion 166 houses scaffold 160. Intermediate portions 164 and 166 is a reduced diameter portion 168 which houses plug assembly 154. Provided at one end of forward portion 166 is an annular shaped porous distribution frit 170, the central opening 170a of which aligns both with plug 156 and also with a generally cylindrically shaped plug receiving cavity 160a formed in scaffold 160. A second porous distribution frit 172 is provided at the opposite end of forward container portion 166 so that scaffold 160 is disposed between the two porous frits. As before, a pierceable septum assembly 174 sealably closes the forward end of the container subassembly and is held in place by a crimp ring 176 which circumscribes a connector ring 177, which is, in turn, sealably connected to portion 166. Septum assembly 174 comprises a forward portion 175a and a body portion 175b which may be of the same or different material as, for example, rubber, silicone or other barrier elastomers, and includes a permeability barrier 175c. The container of this latest form of the invention is preferably constructed from glass, while the crimp ring is a formable metal such as aluminum and the connector ring is preferably plastic, such as polyvinyl chloride, polypropylene and nylon.

In using the apparatus of this latest form of the invention, with the fill assembly in the filled configuration, the cover subassembly is first removed from the container subassembly in the manner previously described. In this regard, the cover subassembly of the fill assembly, while not shown in FIG. 20, is identical to that shown in FIG. 3 and includes a spiral-wound, frangible portion 58 and a cylindrical portion 64. By pulling on pull-tab 60 of the spiral-wound portion 58, portion 58 can be torn away from the container subassembly so that it can be separated from the forwardly disposed portion 64. Once the spiral-wound portion 58 is removed, cylindrical portion 64 can also be removed and discarded placing the assembly in the configuration shown in FIG. 20 enabling it to be mated with the syringe assembly in the manner shown in FIG. 22.

Mating of the adapter subassembly with the syringe assembly is accomplished by telescopically inserting the exposed container portion of the container subassembly into chamber 70 and pushing the assemblage forwardly as shown in FIG. 22 causing a piercing cannula 180 to pierce septum 174. As the adapter subassembly moves forwardly, plunger 42 will exert a force on the fluid "F" contained within fluid chamber 152 causing plug 158 of the flow control means to move from the fluid flow blocking position shown in FIG. 20 into the open position shown in FIG. 22 wherein the plug is seated within cavity 160a. Further movement of the adapter subassembly inwardly of chamber 70 will cause the fluid "F" to flow through the central passageway of plug 156, through frit 170 and around, about and through the adding means. Following expulsion of the fluid "F" from chamber 152, plunger 42 will seat against plug assembly 154. It is to be noted that piercing cannula 180 which is carried by a wall 182 of a delivery adapter subassembly 184, which is connected to the forward end of the syringe body, functions to provide a fluid flow path between fluid chamber 152 and the exterior of the apparatus via porous frit 172 and septum chamber 174c. The adding means which comprises additives of the scaffold 160 function to controllably add to the fluid "F" selected beneficial agents as it flows through the adding means.

Figure 23:
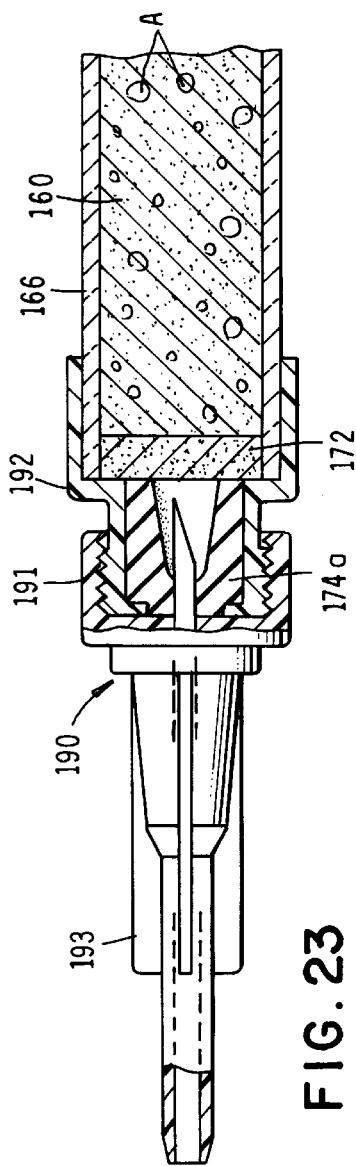
FIG. 23 is a fragmentary, cross-sectional view of the end portion of still another alternate form of apparatus of the invention.

Referring next to FIG. 23, an alternate end construction is there shown. The apparatus shown in FIG. 23 is similar in construction and operation to the embodiment shown in FIG. 20, save that the forward portion of the container subassembly is of a unique design which permits a novel coupling assembly 190 to be interconnected with the container assembly. In this regard, an externally threaded, generally cylindrically shaped coupling ring 192 is connected to the forward container portion 166 which is of the same general character previously described and functions to secure in place a septum 174a. Coupling assembly 190 includes a generally cylindrically shaped, threaded ring 191 which can be threadably mated with coupling 192. Ring 191 supports a blunt end cannula 193 of the character shown in FIG. 23, which can, for example, be used to penetrate a slit septum carried within the inlet port of a fluid dispensing device. Ring 191 can be constructed from various materials including metal and plastic.

Figure 24:
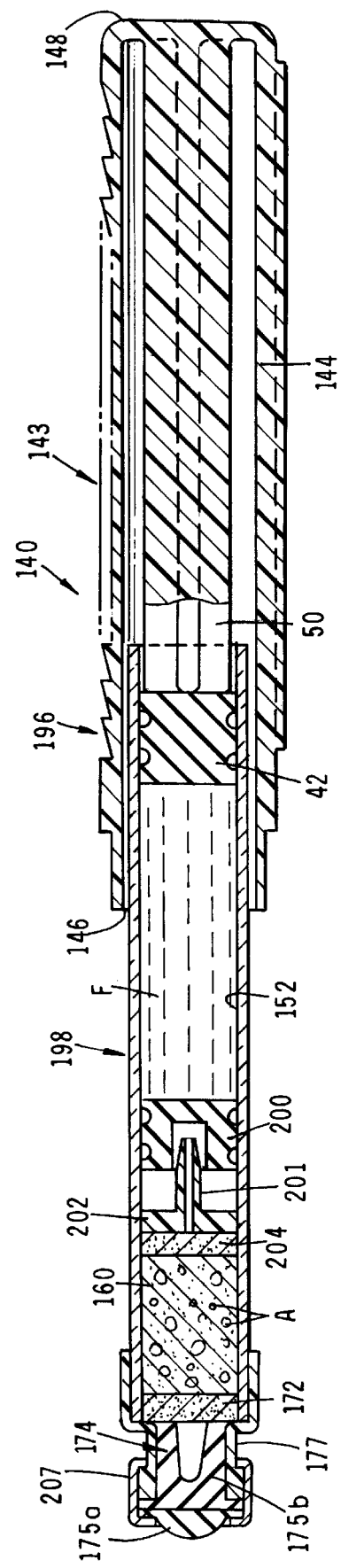
FIG. 24 is an enlarged, cross-sectional view of yet another embodiment of the container and adapter subassemblies of the fill assembly of the present invention.

Another form of adapter and container subassembly of the invention is shown in FIG. 24 and is generally designated by the numeral 196. Subassembly 196 is similar in many respects to that shown in FIG. 20 and like numbers are used to identify like components. Subassembly 196 here comprises an adapter subassembly 143 which includes a hollow housing 144 having a first open end 146 and a second closed end 148 (FIG. 24). A container subassembly 198 is telescopically receivable within open end 146 of housing 144 in the manner shown in FIG. 24 so that the housing can be moved from an extended position shown in FIG. 24 to an advanced position. As before, the adapter subassembly includes pusher means shown here as an elongated pusher rod 50 which functions to move plunger 42 within fluid chamber 152 from the first position shown in FIG. 24 to an advanced position wherein the plunger seats against an alternate type of flow control means. This alternate flow control means is here provided as a pierceable plug 200. Plug 200 is generally cylindrically shaped and is adapted to be pierced by a piercing cannula 201 which is carried by a partition wall 202 that abuts a porous glass, plastic, or metal frit 204. Plug 200 can be urged forwardly of fluid chamber 152 by fluid pressure generated by the forward movement of plug 42 from the position shown in FIG. 24 to an advanced position wherein cannula 201 pierces the plug thereby permitting fluid "F" to flow from fluid chamber 152 toward porous distribution frit 204 and then around, about and through scaffold 160 which has an additive "A" removably affixed thereto. As before a second porous distribution frit 172 is provided at the opposite end of container subassembly 198 so that scaffold 160 is disposed between glass frits 172 and 204. A pierceable septum 174 sealably closes the forward end of the container subassembly and is held in place by a crimp ring 207 which circumscribes a connector ring 177 which is, in turn, sealably connected to container assembly 198.

Figure 25:
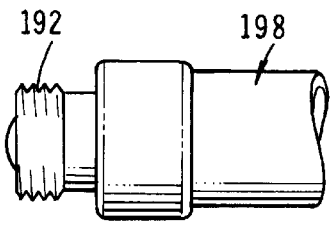
FIG. 25 is a fragmentary, side-elevational view of the forward portion of an alternate form of the container subassembly of the present invention.
Figure 26:
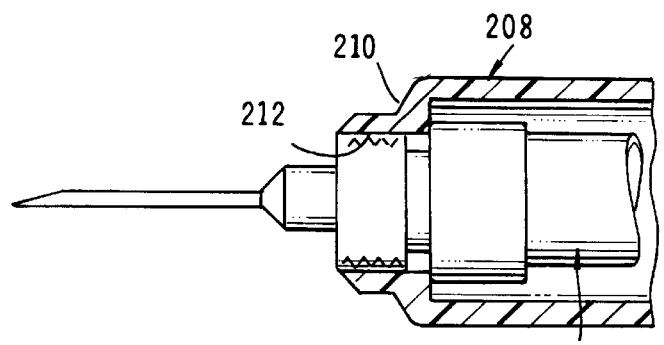
FIG. 26 is a fragmentary, cross-sectional view of the forward end portion of an alternate form of the syringe assembly of the present invention showing the container subassembly mated therewith.
Figure 27:
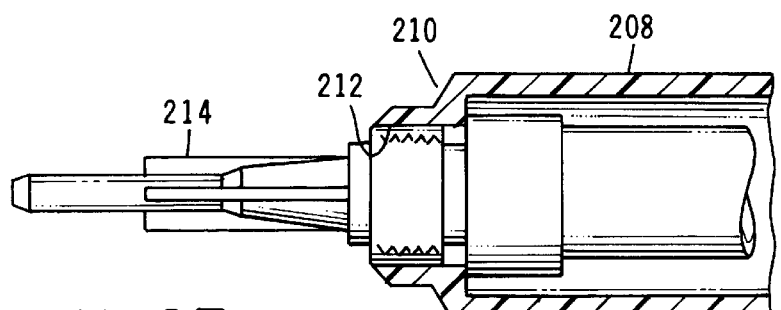
FIG. 27 is a fragmentary, cross-sectional view of an alternate form of the apparatus of the invention showing the container subassembly mated with the syringe subassembly of the invention.

For certain applications, the container assembly shown in FIG. 24 can be provided with an externally threaded coupling ring 192 of the character shown in FIG. 23 thereby enabling the interconnection of a variety of cannula adapter assemblies (see also FIG. 25). However to accommodate these assemblies, a syringe assembly of a slightly different configuration must be provided. Such syringe assemblies are shown in FIGS. 26 and 27. These modified syringe assemblies, which are generally designated by the numeral 208, include a forward portion 210 which has a central opening 212 that is of a size to accommodate the various cannula assemblies.

Figure 28:
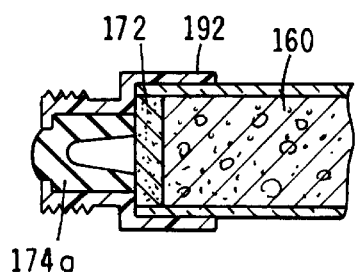
FIG. 28 is a fragmentary, cross-sectional view of the forward portion of another embodiment of the container subassembly of the invention.
Figure 29:
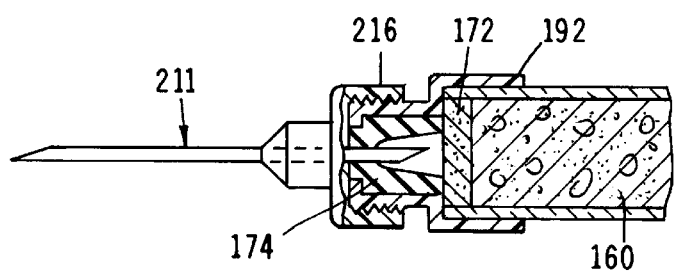
FIG. 29 is a fragmentary, cross-sectional view similar to FIG. 28 but showing a cannula assembly interconnected with the container subassembly shown in FIG. 28.
Figure 30:
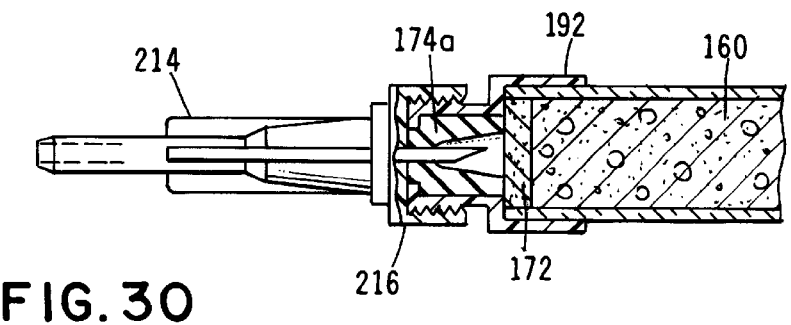
FIG. 30 is a fragmentary, cross-sectional view similar to FIG. 29 but showing an alternate form of cannula assembly interconnected with the container subassembly shown in FIG. 28.

Turning particularly to FIGS. 28 and 29, FIG. 28 shows in cross section the forward portion of a container subassembly which has been provided with a threaded coupling ring 192. Coupling ring 192 is adapted to threadably receive either the conventional needle type cannula assembly 211 shown in FIG. 29 or, alternatively, the blunt end type cannula assembly 214 shown in FIG. 30. Since both of these assemblies are provided with the threaded adapter ring 216, which will threadably mate with the threaded coupling ring 192 of the container subassembly, either cannula assembly can be readily connected to the container subassembly in the manner shown in FIGS. 29 and 30. As illustrated in FIGS. 26 and 27, the assemblages thus formed can be mated with the modified syringe assemblies 208.

Still another alternate construction of the fluid containing assembly is shown in FIGS. 31 and 35 and generally designated by the numeral 220. The apparatus shown in these figures is similar in construction and operation to the embodiment shown in FIG. 24, save that a different type of flow control means is provided.

As before, fluid containing assembly 220 here comprises an adapter subassembly 143 which includes a hollow housing 144 having a first open end 146 and a second closed end 148 (FIG. 31). A container subassembly 222 is telescopically receivable within open end 146 of housing 144 in the manner shown in FIG. 31 so that the housing can be moved from an extended position shown in FIG. 31 to an advanced position shown in FIG. 35. Adapter subassembly 143 includes pusher means shown here as an elongated pusher rod 50 which functions to move plunger 42 within fluid chamber 224 from the first position shown in FIG. 31 to an advanced position wherein the plunger rests against the previously mentioned, alternate type of flow control means. This alternate flow control means is here provided in the form of an elastomeric silicone or rubber plug 226. Plug 226, which includes a permeability barrier 226a, is generally cylindrically shaped and is adapted to be sealably received within a chamber 228 formed by a necked-down portion 230a of the outer wall of a container 230 which comprises a part of container subassembly 222. Plug 226 can be urged forwardly of chamber 228 by fluid pressure generated by the forward movement of plug 42 from the position shown in FIG. 31 to an advanced position wherein it is received within a forward fluid bypass chamber 232. As shown in FIGS. 31, 34 and 35, chamber 232 is provided with a plurality of longitudinally extending, circumferentially spaced ribs 234 which form therebetween fluid bypass channels 236. With this construction, when plug 226 is moved by fluid pressure into chamber 232, in the manner shown in FIG. 35, it will move into seating engagement with spline-like plug stops 238 (FIG. 32). With the plug thus resting in its forward position, fluid can flow past the plug via channels 236, toward porous distribution frit 204 and then around, about and through scaffold 160 to which an additive "A" has been removably affixed. The novel construction of the spline-like plug stops, including the integral spline end portions thereof, preclude plug over travel and insure proper flow distribution toward distribution frit 204. As before a second porous distribution frit 172 is provided at the opposite end of container subassembly 222 so that scaffold 160 is disposed between porous frits 172 and 204. A pierceable septum assembly 174 sealably closes the forward end of the container subassembly and is held in place by a crimp ring 207 which circumscribes a connector ring 177 which is, in turn, sealably connected to container subassembly 222.

Turning now to FIGS. 36 and 37, another form of the fluid containing assembly is there shown and generally designated by the numeral 244. The apparatus shown in these figures is similar in construction and operation to the embodiment shown in FIGS. 31 through 35, save that the container assembly 246 includes a container 248 having dual fluid chambers or reservoirs 250 and 252. Disposed between chambers 250 and 252 is a novel fluid expelling means, which will be described in greater detail hereinafter, comprising a fluid-expandable material 254 which is contained within an intermediate third chamber 256. The fluid expelling means here forms a part of the fluid flow control means of the invention and when exposed to a swelling agent, functions to expel fluid from the forward most of the dual chambers.

As before, the fluid containing assembly 244 comprises an adapter subassembly 143 which includes a hollow housing 144 having a first open end 146 and a second closed end 148 (FIG. 36). (Once again like numbers are used in FIGS. 36 and 37 to identify like components.) The modified container subassembly 246 is telescopically receivable within open end 146 of housing 144 in the manner shown in FIG. 36 so that the housing can be moved from an extended position shown in FIG. 36 to an advanced position shown in FIG. 37. Adapter subassembly 143 includes pusher means shown here as an elongated pusher rod 50 which, as before, functions to move plunger 42 within the inboard fluid chamber 250 from the first position shown in FIG. 36 to an advanced position wherein the plunger seats against a portion of the alternate type of flow control means. In addition, to the fluid expelling means, the alternate flow control means of this latest form of the invention also includes the previously identified elastomeric plug 226 which is adapted to be sealably received within a chamber 257. Chamber 257 is of similar construction to chamber 228 shown in FIG. 31 and is formed by a necked-down portion of the outer wall of a container 248. Plug 226 can be urged forwardly of the inboard fluid chamber 250 by fluid pressure generated by the forward movement of plug 42 from the position shown in FIG. 36 to the advanced position shown in FIG. 37 wherein it is received within a forward fluid bypass chamber 260. Chamber 260 is of identical construction to chamber 232 shown in FIGS. 31, 32, and 34 and is provided with a plurality of longitudinally extending, circumferentially spaced ribs 234 which form therebetween fluid bypass channels 236. With this construction, when plug 226 is moved by fluid pressure into chamber 232, in the manner shown in FIG. 37, it will move into seating engagement with spline-like plug stops 238 which are identical to those shown in FIG. 32. With the plug thus seated, fluid can flow past the plug via channels 236 (see also FIG. 34), toward a porous distribution frit 262 which abuts the spline-like plug stops. As before, the novel construction of the spline-like plug stops, including the integral spline end portions thereof, preclude plug over-travel and insure proper flow distribution toward distribution frit 262.

After the fluid contained within inboard chamber 250 flows through distribution frit 262, it will enter intermediate third chamber 256 which contains the fluid-expandable material 254. This causes the material to controllably expand so as to exert a uniform pressure on a fluid expelling plug 264 which is sealably mounted within forward chamber 252 and is telescopically movable therewithin from a first position shown in FIG. 36 to a second position shown in FIG. 37.

Fluid-expandable material 254 is a shaped article here formed into a generally cylindrical shape having an outer peripheral portion 254a which when hydrated, expands to form an expanded member of the character shown in FIG. 37 having a multiplicity of integrally formed open cell voids or pores 254b. Voids 254b permit a swelling agent, such as an aqueous solvent to be uniformly distributed through the peripheral portion of the shaped article causing more controllable longitudinal swelling thereof. The shaped article can be formed in various ways including rolling a miscible blend of hydrophillic and hydrophobic thermoplastic film material into an elongated loosely wound helicoid. This permits the swelling agent to flow freely and uniformly through the shaped article. Material 254 is preferably a swellable polymer, which, if physically constrained, will "generate" a new volume and a resultant displacement force vector which can be utilized. Rates of swelling and degree of swelling are variables which can be controlled to varying degrees in order to exploit the swelling behavior of the article and the resulting force vector as a function of time. Although these principles apply in general to polymers and any appropriate swelling agents, water swollen polymers are customarily termed hydrogels with the unswollen material known as xerogel. Any polymer with an affinity for a swelling agent will absorb that agent and begin the swelling process. The critical requirement for hydrogel formation is the fact that controlled swelling can occur, while dissolving of the polymer does not. Several mechanisms exist to prevent dissolution of the polymer, the simplest and most common being the existence of chemical crosslinkages which create an insoluble network. The chemical crosslinking of an otherwise water soluble polymer leads to hydrogel properties, with the degree of chemical crosslinking being a primary variable in controlling the maximum degree of swelling available at equilibrium. Examples of such materials are formaldehyde-crosslinked gelatin used in photographic films, or polyhydroxyethylmethacrylate crosslinked with ethylene glycol dimethacrylate as used in many hydrogel contact lenses. The disadvantage of such materials is that the network character precludes other processing methods such as melt molding, extrusion, etc. since the crosslinked network structures are unable to flow when heated.

Pseudocrosslinks may be created in other ways than by the use of chemical agents. For example, xerogels which are themselves semicrystalline polymers, present the possibility that the amorphous regions of such polymers will be more susceptible to swelling than will be the crystalline regions. If the crystalline regions of such materials is in fact insoluble at the swelling temperature, it acts identical to a chemical crosslink and prevents dissolution of the swollen material. Here, the degree of crystallinity is analogous to the amount of chemical crosslinker employed in the first type above. There are few examples of water swellable semicrystalline polymer materials; one of these is polyvinylalcohol (PVA) and its copolymers. In this case the degree of crystallinity of the PVA materials is inversely related to the water swell, i.e., the higher the extent of crystallinity of the PVA, the lower the water swell. Crystallinity can be controlled by a number of factors, including polymer chemical composition, tactic (stereochemical) order, thermal processing/annealing conditions, etc. The fact that these types of hydrogels or xerogels are not chemically crosslinked allows for the possibility that the materials can be processed and fabricated into components or products using conventional high speed manufacturing processes such as extrusion molding and the like.

Another approach to non-chemically crosslinked xerogels and hydrogels is the use of polymer blends of hydrophilic polymers with hydrophobic polymers. If one identifies or selects pairs of such polymers, one hydrophilic and one hydrophobic, in which the unswollen polymers form a thermodynamically miscible, single phase blend or alloy, this xerogel material can be swollen in water to make a hydrogel whose water swell level is roughly proportional to the weight fraction of the hydrophilic polymer in the blend xerogel. These materials are not chemically crosslinked and thus can be processed via conventional melt processing methods, leading to manufacturing efficiencies, improved costs, and product forms unattainable from crosslinked materials. Several combinations of such polymers ("miscible blend hydrogels") exist. In this regard, reference should be made to U.S. Pat. No. 4,771,089 issued Sep. 13, 1988 to Ronald F. Ofstead. Due to the pertinence of this patent, it is hereby incorporated by reference as though fully set forth herein. Exemplary of materials which can be used in such an approach are as follows:

| Hydrophilic Thermoplastic | + Hydrophobic Thermoplastic |
|---|---|
| Poly-N-vinylpyrrolidone | Phenoxy Resin |
| Poly-N-dilmethylacrylamide | Sulfone Resin |
|  | Cellulose Acetate |

-continued

| Hydrophilic Thermoplastic | + Hydrophobic Thermoplastic |
|---|---|
|  | Polyvinylidene Fluoride |
|  | Polyacrylonitrile |
|  | Polycarbonate |
|  | Polymethylmethacrylate |
|  | Butvar Resin |
|  | Soluble Polyimides |
|  | Vinyl Chloride Copolymers |
|  | Polybenzylmethacrylate |

It is to be appreciated that the fluid expandable material can be configured in many different geometric forms with fluid flow interstitial passageways formed by a number of methods well known to those skilled in the art. The expandable material can comprise a single component or, alternatively, an assemblage made up of a variety of components of various miscible blend, swellable materials each having different volumes and swelling ratios to provide varying differential displacement vectors as a function of time. Certain of the components which make up assemblage 154 can also be configured to act as fluid flow central gates to enable pulsed delivery. In this instance the gate forming components do not expand, but rather transmit the swelling agents to the next component.

As before, pierceable septum assembly 174 sealably closes the forward end of the container subassembly and is held in place by a crimp ring 207 which circumscribes a connector ring 177 which is, in turn, sealably connected to container subassembly 246.

The fluid containing subassembly shown in FIGS. 36 and 37 is, of course, mateable with a syringe assembly in the manner previously described herein so that fluid can be delivered from the device via cannula means generally designated in FIG. 37 by the numeral 267.

Still another form of the apparatus of the invention is shown in FIGS. 38 through 45. The apparatus shown in these figures is similar in construction and operation to the embodiment shown in FIGS. 36 and 37, save that the syringe assembly is of a slightly different, two-piece construction. On the other hand, the container assembly is of almost identical construction to that shown in FIGS. 36 and 37, but here includes at its forward end a quick coupling receiver means rather than a pierceable syringe. The quick coupler receiver means comprises a part of the delivery means of this form of the invention and enables interconnection of a quick coupler and fluid delivery cannula with the container assembly so that fluid from the forward most of dual fluid chambers formed in the fluid container can be controllably delivered from the apparatus via the delivery cannula. As before, the container assembly comprises a container 272 having dual fluid chambers or reservoirs 274 and 276. Disposed between chambers 274 and 276 is a novel fluid expelling means, which comprises a fluid-expandable material 254 of the character previously described that is contained within an intermediate third chamber 278. Once again, the fluid expelling means forms a part of the fluid flow control means of the invention and when exposed to an expanding agent, functions to expel fluid from the forward most of the dual chambers.

Figure 41:
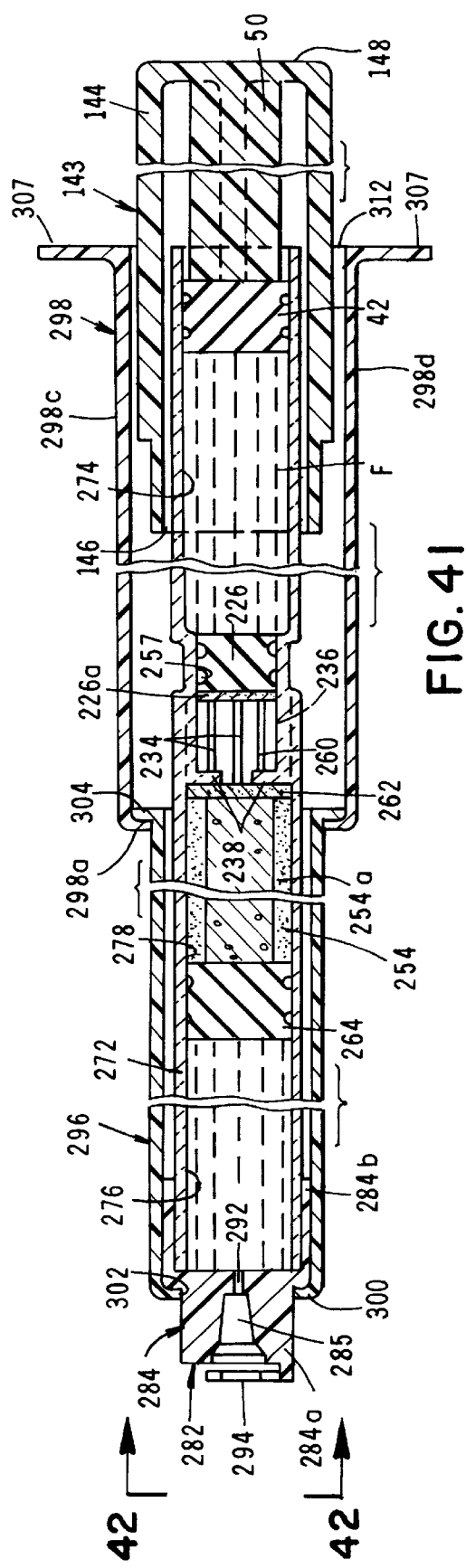
FIG. 41 is a side-elevational, cross-sectional view of yet another form of the container and adapter subassemblies of the fill assembly of the invention mated with the alternate form of syringe assembly shown in FIGS. 38 and 39.

As best seen in FIG. 41, the fluid containing assembly comprises an adapter subassembly 143 which includes a hollow housing 144 having a first open end 146 and a second closed end 148. (As before, like numbers have been used in FIGS. 38 through 45 to identify like components.) The modified container subassembly is telescopically receivable within open end 146 of housing 144 in the manner shown in FIG. 41 so that the housing can be moved from an extended position shown in FIG. 41 to an advanced position shown in FIG. 43. The adapter subassembly 143 includes pusher means shown here as an elongated pusher rod 50 which functions to move plunger 42 within the inboard fluid chamber 274 from the first position shown in FIG. 41 to an advanced position wherein the plunger seats against a portion of the alternate type of flow control means. In addition, to the fluid expelling means, the alternate flow control means of this latest form of the invention also includes the previously identified elastomeric plug 226 which is adapted to be sealably received within a chamber 257. Chamber 257 is of similar construction to chamber 228 shown in FIG. 31 and is formed by a necked-down portion of the outer wall of a container 272. Plug 226 can be urged forwardly of chamber 257 by fluid pressure generated by the forward movement of plunger 42 from the position shown in FIG. 41 to the advanced position shown in FIG. 43 wherein it is received within a forward fluid bypass chamber 260. Chamber 260 is of identical construction to chamber 232 shown in FIGS. 31, 32, and 34 and is provided with a plurality of longitudinally extending, circumferentially spaced ribs 234 which form therebetween fluid bypass channels 236. With this construction, when plug 226 is moved by fluid pressure into bypass chamber 260, in the manner shown in FIG. 37, it will move into seating engagement with spline-like plug stops 238 which are identical to those shown in FIG. 32. With the plug thus seated, fluid can flow past the plug via channels 236 (see also FIG. 34), toward a porous distribution frit 262 which abuts the spline-like plug stops. As before, the novel construction of the spline-like plug stops, including the integral spline end portions thereof, preclude plug over travel and insure proper fluid flow distribution toward porous distribution frit 262.

After the fluid contained within inboard chamber 274 flows through distribution frit 262, it will enter intermediate third chamber 278 which contains the fluid-expandable material 254. As previously described, this causes the material to controllably expand so as to exert a uniform pressure on a fluid expelling plug 264 which is sealably mounted within forward chamber 276 and is telescopically movable therewithin from a first position shown in FIG. 41 to a second position shown in FIG. 43. Hydro-expandable material 254 is of the same character as previously described herein.

As previously mentioned, the pierceable septum assembly 174 shown in FIGS. 36 and 37 has been replaced in this latest embodiment of the invention by means for allowing the quick interconnection of a cannula type delivery means. To this end, provided at the forward most portion of container 272, is the previously mentioned quick coupling receiver means which here comprises an assemblage 282 (FIG. 41). Assemblage 282 includes a housing 284 having a body portion 284a and a skirt portion 284b which is adapted to be sealably received over the forward end of container 272. Body portion 284a is provided with a tapered outlet cavity 285 which is adapted to sealably receive a quick connect delivery fitting 288 that comprises a part of the fluid delivery means of the invention. Fitting 288 includes a tapered inboard end portion 288a and a body portion 288b. A central bore 289 extends through portions 288a and 288b and communicates at its outboard end with a cannula 290 which also forms a part of the delivery means of the invention for delivering fluids from the device (see FIGS. 41, 43, and 45). When fitting 288 is seated within chamber 285, the inboard end of bore 289 communicates with a stub passageway 292 formed in body portion 288b so that fluid can flow from chamber 276 into central bore 289 and then into cannula 290.

Figure 42:
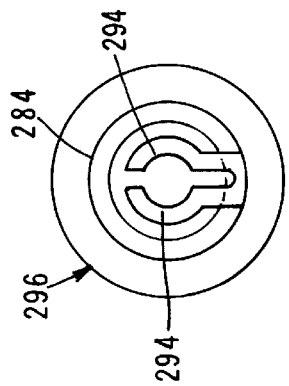
FIG. 42 is a cross-sectional view taken along lines 42—42 of FIG. 41.
Figure 43:
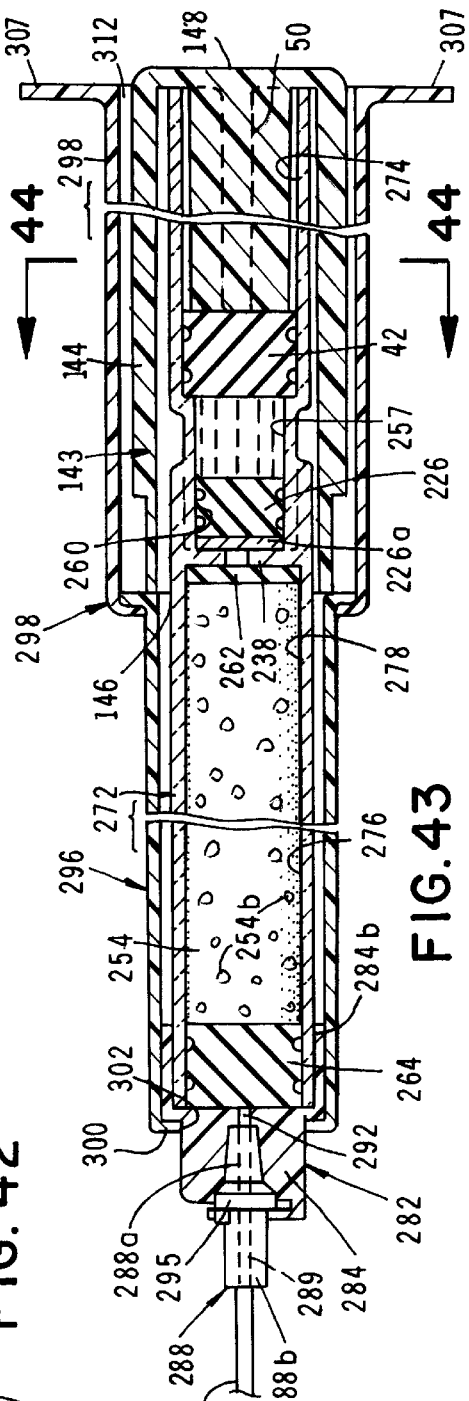
FIG. 43 is a fragmentary side-elevational, cross-sectional view of the apparatus shown in FIG. 41 illustrating the position of the various component parts of the device at the completion of the fluid delivery step.

In order to lock quick connect delivery fitting 288 in the fluid delivery position, locking means shown here as resiliently deformable, generally "C" shaped, locking ears 294 are provided on the body portion 284a of housing 284 (FIG. 42). Ears 294 lockably engage a locking flange 295 provided on fitting 288 (FIGS. 43 and 45). Upon pushing inwardly on fitting 288, ears 294 will yieldably deform outwardly so that tapered portion 288a of the fitting can be sealably introduced into cavity 285. As the fitting seats within the cavity, the resiliently deformable locking ears will lockably engage flange 295 in a manner to lockably interconnect the fitting with housing 284. To remove the fitting, the fitting is turned manually by grasping flats 288c provided thereon. This causes a cam surface 295a provided on flange 295 to spring ears 294 outwardly to permit withdrawal of the fitting from cavity 285.

In using the apparatus of this latest form of the invention, with the fill assembly in the filled configuration, the cover subassembly is first removed from the container subassembly in the manner previously described. In this regard, the cover subassembly of the fill assembly, while not shown in FIGS. 38 through 45 is identical to that shown in FIG. 3 and includes a spiral-wound, frangible portion 58 and a cylindrical portion 64. By pulling on pull-tab 60 of the spiral-wound portion 58, portion 58 can be torn away from the container subassembly so that it can be separated from the forwardly disposed portion 64. Once the spiral-wound portion 58 is removed, cylindrical portion 64 can also be removed and discarded placing the assembly in condition to be mated with the syringe assembly in the manner shown in FIG. 41.

As previously mentioned, the syringe assembly is of a slightly different construction and, as shown in FIGS. 38, 39, and 40, comprises a forward portion 296 and an enlarged diameter rearward portion 298, which portions are interconnected in the manner shown in FIG. 39. Forward portion 296 includes a forward wall 300 having an aperture 302 which is sized to closely receive body portions 284 of assemblage 282 (see FIG. 41). An out-turned connector flange 304 is provided at the opposite end of forward portion 296 for interconnection with an in-turned flange 298a provided in rear portion 298 (FIG. 39) as by adhesive bonding, sonic welding or any other suitable process.

Rearward portion 298 has oppositely disposed, generally flat side walls 298b which are interconnected by top and bottom curved walls 298c and 298d (FIG. 44). Also provided on portion 298 are outwardly extending finger engaging tabs 307 which can be gripped by the user during the advancement of piston 42 within chamber 274 of the container.

Mating of the adapter subassembly with the syringe assembly is accomplished by telescopically inserting the exposed container portion of the container subassembly into forward portion 296 in the manner shown in FIG. 41. As the assemblage is move forwardly, body 284 of assemblage 282 will be received within aperture 302 and the container assembly will seat against wall 300. In this position a portion of the adapter assembly 143 extends outwardly from the rearward portion 298 of the syringe assembly. By pushing the adapter assembly inwardly, pusher rod 50 will engage plunger 42 moving it forwardly of chamber 274. As the plunger moves forwardly, it will exert a force on the fluid "F" contained within fluid chamber 274 causing plug 226 of the flow control means to move from the fluid flow blocking position shown in FIG. 41 into the open position shown in FIG. 43 wherein the plug is seated within bypass chamber 257. With plug 226 seated within chamber 257, the fluid "F" will flow through flow channels 236, through frit 262, and into contact with the fluid-expandable material 254. As shown in FIG. 41, the fluid-expandable material 254 is formed into a generally cylindrically shaped member having an outer peripheral portion 254a which when exposed to swelling agents, expands to form an expanded member of the character shown in FIG. 43 having a multiplicity of pores 254b. As previously discussed, material 254 is preferably a swellably polymer, which, if physically constrained, will "generate" a new volume and a resultant force vector which can be utilized. In this instance, following the attachment of the quick connector assembly 288 to the container assembly, the force vector is used to urge plunger 264 forwardly of chamber 276. This will controllably urge the fluid contained within chamber 276 to flow outwardly of the device via delivery cannula 290. It is to be understood that various valving arrangements well known to those skilled in the art can be used to regulate fluid flow through delivery cannula 290 and outwardly toward a patient.

In order to securely lock the adapter subassembly with the syringe assembly after mating thereof has been accomplished, locking means are provided. As before, the locking means here comprise a series of locking teeth which are constructed so that they will slide under a flexible locking tab 311 (FIGS. 38 and 39) which is provided proximate the entrance of chamber 312 of syringe housing, as the adapter subassembly is urged inwardly of chamber 312 (FIG. 41). However, once the adapter subassembly has reached the fully forward position shown in FIG. 43, locking tab 311 will engage one of the teeth and effectively prevent removal of the housing 144 of the adapter subassembly from chamber 312. With this novel construction, once the adapter assembly is mated with the syringe housing, it cannot be removed therefrom thereby preventing system reuse or adulteration.

Figure 47:
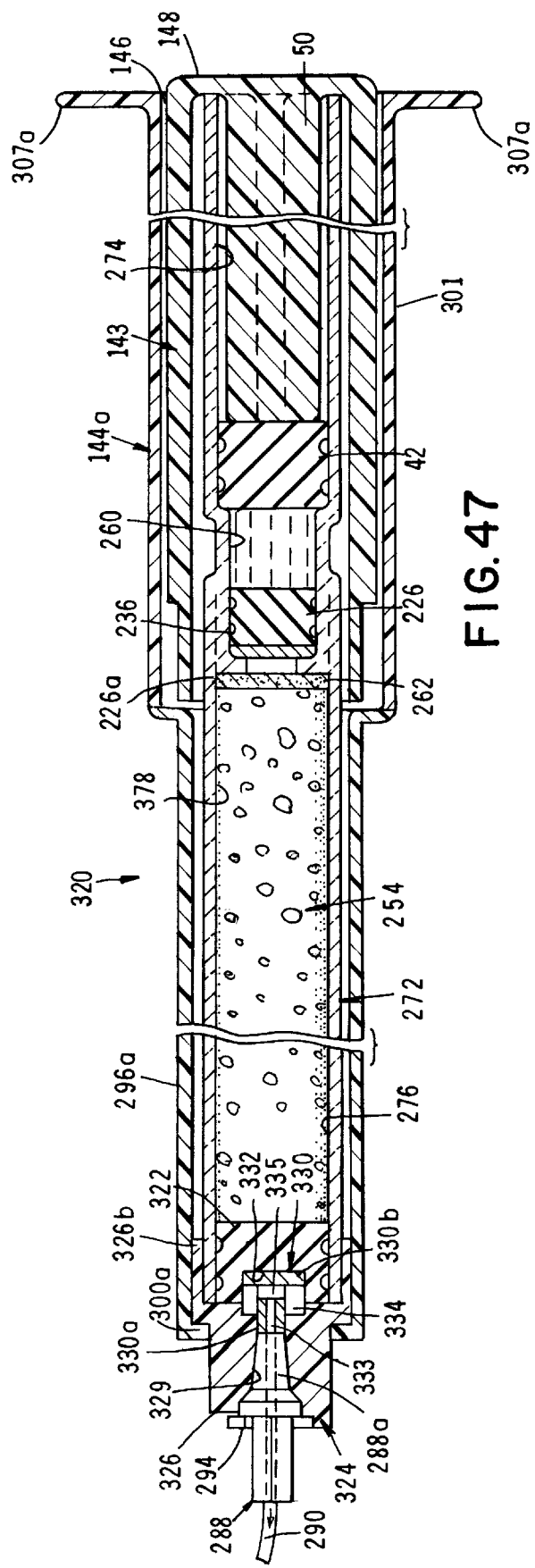
FIG. 47 is a fragmentary side-elevational, cross-sectional view of the apparatus shown in FIG. 46 illustrating the position of the various component parts of the device at the completion of the fluid delivery step.
Figure 48:
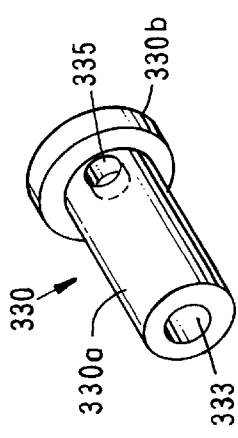
FIG. 48 is a generally perspective view of the chuck valve means of this latest embodiment of the invention.

Referring to FIGS. 46, 47, and 48, still another form of the apparatus of the invention is there shown and generally designated by the numeral 320. This apparatus is similar in construction and operation to the embodiment shown in FIGS. 41 and 43, save that the syringe assembly is of a one-piece construction and the quick coupler receiving means of the device is provided with novel check valve means for controlling fluid flow from the device. The container assembly is otherwise of almost identical construction to that shown in FIGS. 41 and 43 and includes at its forward end a quick coupling receiver means of the character previously described to enable interconnection of a quick coupler and fluid delivery cannula with the container assembly. As will presently be described, the quick coupler functions to open the check valve means upon its interconnection with the quick coupler receiving means. As before, the container assembly comprises a container 272 having dual fluid chambers or reservoirs 274 and 276 (like numbers being used to identify like components). Disposed between chambers 274 and 276 is a novel fluid expelling means, which comprises a fluid-expandable material 254 of the general character previously described that is contained within an intermediate third chamber 278. Once again, the fluid expelling means forms a part of the fluid flow control means of the invention and when exposed to a swelling agent, functions to expand volumetrically and displace the fluid from the forward most of the dual chambers. However, the fluid expelling means here comprises a plurality of portions 254a, 254b, 254c, and 254d (FIG. 46), each of which exhibits a different expansion characteristic when exposed to the swelling agent.

Accordingly, the expelling means can here function to provide various predetermined pattern delivery protocols. More particularly, the fluid delivery can be accomplished in accordance with a precise, predetermined pattern of selected rates and volumes, including pulsed and non-pulsed delivery.

The modified container subassembly is telescopically receivable within open end 146 of a one-piece housing 144a in the manner shown in FIG. 46 so that the housing can be moved from an extended position shown in FIG. 46 to an advanced position shown in FIG. 47. Once again, the adapter subassembly 143 includes pusher means shown here as an elongated pusher rod 50 which functions to move plunger 42 within the inboard fluid chamber 274 from the first position shown in FIG. 46 to an advanced position wherein the plunger seats against a portion of the previously considered alternate type of flow control means as described in connection with FIG. 41.

After the fluid contained within chamber 274 flows through the flow control means and then through distribution frit 262, it will enter intermediate third chamber 278. This fluid, which acts as the expanding agent, will impinge on the various material portions 254a, 254b, 254c, and 254d causing them to selectively expand in a manner to exert a tailored pressure on a plunger 322. Plunger 322, which is of a slightly modified construction, is sealably mounted within forward chamber 276 and is telescopically movable therewithin from a first position shown in FIG. 46 to a second position shown in FIG. 47. More particularly and by way of example, portion 254a of the fluid-expandable material 254 can be tailored to expand in a manner to provide a first delivery volume of beneficial agent at a first delivery rate, while portion 254b can be tailored to expand in a manner to provide a second delivery volume of beneficial agent at a second delivery rate.

As was the case in the last described embodiment of the invention, the pierceable septum assembly 174 shown in FIGS. 36 and 37 has been replaced by means for allowing the quick interconnection of a cannula type fluid delivery means of the invention, which functions to deliver fluid from the apparatus. To this end, provided at the forward most portion of container 272, is a quick coupling receiver means which here comprises an assemblage 324 (FIG. 46). Assemblage 324 includes a housing 326 having a body portion 326a and a skirt portion 326b which is adapted to be sealably received over the forward end of container 272. Body portion 326a is provided with a generally cylindrically shaped portion 328 and a tapered outlet cavity 330 which sealably receives the previously identified quick connect delivery fitting or fluid administration line coupler 288.

Receivable within cylindrically shaped portion 328 is the generally cylindrically shaped hollow body portion 330a of the previously mentioned check valve means, which here comprises a part of the fluid flow control means of the invention for controlling fluid flow toward the cannula type delivery means.

As best seen in FIG. 48, the check valve 330 of the check valve means includes, in addition to body portion 330a, an enlarged diameter portion 330b which is closely receivable both within a cavity 332 formed in plug 322 (FIG. 47) and within a cavity 334 formed in housing 326 of assemblage 324. Body portion 330a is also provided with an axial bore 333 and a cross-bore 335 (FIG. 48), the purpose of which will presently be described.

As previously mentioned, the syringe assembly is of a slightly different construction and comprises a forward portion 296a which includes a forward wall 300a having an aperture which is sized to closely receive body portion 326. Rearward portion 298a, like portion 298, has oppositely disposed, generally flat side walls which are interconnected by top and bottom curved walls (FIG. 44). Also provided on portion 298a are outwardly extending finger engaging tabs 307a which can be gripped by the user during the advancement of piston 42 within chamber 274 of the container.

Mating of the adapter subassembly with the syringe assembly is accomplished by telescopically inserting the exposed container portion of the container subassembly into forward portion 296a in the manner shown in FIG. 46. As the assemblage is move forwardly, body 326 of assemblage 324 will be received within the apertured forward wall and the container assembly will seat against wall 300a. In this position a portion of the adapter assembly extends outwardly from the rearward portion 298a of the syringe assembly. By pushing the adapter assembly inwardly, pusher rod 50 will engage plunger 42 moving it forwardly of chamber 274. As the plunger moves forwardly, it will exert a force on the fluid "F" contained within fluid chamber 274 causing plug 226 of the flow control means to move from the fluid flow blocking position shown in FIG. 46 into the open position shown in FIG. 47 wherein the plug is seated within bypass chamber 260. With plug 226 seated within chamber 260, the fluid "F" will flow through flow channels 23b through frit 262, and into contact with the fluid-expandable material 254 causing it to expand.

As the quick connect assembly is interconnected in the manner shown in FIG. 47, portion 288a of the connector will engage valve member 330 of the fluid flow control means moving it from the closed, fluid flow blocking position shown in FIG. 46 into the open position shown in FIG. 47 wherein the enlarged diameter portion 330b enters cavity 332 formed in plug 322.

As previously discussed, the various physically constrained segments, or material portions 254a, 254b, 254c, and 254d of the fluid expelling means, when expanded, will generate force displacement vectors which can be used to controllably urge second plunger 322 forwardly of chamber 276 in a manner to expel the beneficial agent "B" contained therein (FIG. 46) in accordance with a predetermined pattern delivery protocol. As the beneficial agent "B" is urged toward the delivery cannula, it will flow past the open check valve means, or valve 330 via passageways 335 and 333 and then into delivery cannula 290 which is disposed proximate the opening in end wall 300a.

In order to securely lock the adapter subassembly with the syringe assembly after mating thereof has been accomplished, locking means of the character previously described are provided.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A syringe apparatus comprising:
   (a) a syringe assembly including:
      (i) an elongated housing defining an internal chamber; and
      (ii) a cannula means operably associated with said elongated housing for providing a fluid flow path, said cannula means including a hollow cannula having first and second end portions; and
   (b) a fluid containing assembly interconnected with said syringe assembly comprising:
      (i) a container assembly including:
         a. a container having a body portion, a fluid chamber, and first and second ends; and
         b. a plunger telescopically movable within said container from a first location proximate said second end of said container to a second spaced apart location to cause fluid flow toward said cannula means; and
      (ii) an adapter assembly telescopically movable within said internal chamber of said housing of said syringe assembly from a first extended position to a second advanced position, said adapter assembly comprising a hollow housing having walls defining an internal chamber for telescopically receiving said container, said hollow housing including pusher means for moving said plunger of said container assembly toward said second location as said hollow housing of said adapter assembly moves within said syringe assembly from said first extended position to said second advanced position wherein said container is substantially encapsulated within said hollow housing, whereby fluid will flow from said fluid chamber of said container through said fluid flow path.

2. An apparatus as defined in claim 1 in which said hollow housing of said adapter assembly includes a closed end and in which said pusher means comprises a pusher rod connected to said closed end, said pusher rod being engagable with said plunger of said container assembly to move said plunger within said container between first and second locations as said hollow housing of said adapter assembly moves between said first extended position and said second position.

3. An apparatus as defined in claim 1 further including a cover assembly connected to said fluid containing assembly comprising a cover having a first open end for telescopically receiving a part of said body portion of said container of said container assembly and a second end, said cover being removable from said container.

4. An apparatus as defined in claim 1 further including adding means disposed within said body portion of said container for adding an additive to the fluid contained within said fluid chamber.

5. An apparatus as defined in claim 1 in which said container assembly further includes closure means for sealably closing said first end of said container said closure means being pierceable by said first end portion of said hollow cannula.

6. An apparatus as defined in claim 1 in which said syringe assembly further includes locking means for lockably interconnecting said adapter assembly with said syringe assembly.

7. An apparatus as defined in claim 1 in which said second end portion of said hollow cannula extends outwardly from said housing of said syringe assembly and terminates in a piercing extremity.

8. An apparatus as defined in claim 7 further including means for sealably enclosing said second end portion of said hollow cannula.

9. A syringe apparatus comprising:
   (a) a syringe assembly including an elongated housing having side and end walls defining an internal chamber, said end wall having an opening therethrough;

(b) fluid delivery means for delivering fluid from said apparatus including a hollow cannula located proximate said opening in said end wall for providing a fluid flow path to the exterior of the apparatus; and (c) a fluid containing assembly operably associated with said syringe assembly and with said fluid delivery means, said fluid containing assembly comprising:

(i) a container assembly including:
  a. a container having a body portion, including a first fluid containing chamber, a second fluid containing chamber, a third intermediate chamber and first and second ends;
  b. fluid flow control means carried by said container for controlling fluid flow in a direction toward said fluid delivery means, said fluid flow control means comprising fluid expelling means for expelling fluid from said second fluid containing chamber, said fluid expelling means comprising a fluid expandable material; and
  c. a first plunger telescopically movable within said first fluid containing chamber of said container from a first location proximate said first end of said container to a second spaced apart location to cause fluid flow in a direction toward said third intermediate chamber; and (ii) an adapter assembly telescopically movable within said internal chamber of said housing of said syringe assembly from a first extended position to a second advanced position, said adapter assembly comprising:
  a. a hollow housing having a first open end for telescopically receiving a part of said container of said container assembly and a second closed end; and
  b. pusher means for moving said plunger of said container assembly as said adapter assembly moves from said first extended position to said second position.

10. An apparatus as defined in claim 9 in which said fluid-expandable material comprises a hydro-expandable material.

11. An apparatus as defined in claim 9 in which said fluid-expandable material is expandable by a fluid-expanding agent which expands said material in a manner to generate a resultant force vector usable for expelling fluid from said second fluid containing chamber.

12. An apparatus as defined in claim 11 in which said fluid-expandable material comprises a shaped article having interstitial flow distribution means for distributing said fluid-expanding agent throughout at least a portion of said shaped article.

13. An apparatus as defined in claim 12 in which said shaped article comprises a plurality of portions each exhibiting different expansion characteristics.

14. An apparatus as defined in claim 13 in which said shaped article, when expanded, provides for a predetermined pattern delivery protocol of said fluid contained within said second fluid containing chamber.

15. An apparatus as defined in claim 13 in which said shaped article when expanded provides a first delivery volume at a first delivery rate and a second delivery volume at a second delivery rate of said fluid contained within said second fluid containing chamber.

16. An apparatus as defined in claim 15 in which said shaped article contains portions which enable pulsed delivery of said fluid contained within said second fluid containing chamber.

17. A syringe apparatus comprising:
(a) a syringe assembly including:
  (i) an elongated housing having side and end walls defining an internal chamber, said end wall having an opening; and
  (ii) a hollow cannula disposed within said opening in said elongated housing and extending into said internal chamber thereof, said hollow cannula defining a fluid outlet passageway; and (b) a fluid containing assembly operably interconnectable with said syringe assembly comprising:
  (i) a container assembly including:
    a. a container having a body portion, a fluid chamber, and first and second ends;
    b. closure means for sealably closing one end of said container; and
    c. a plunger telescopically movable within said container from a first location proximate one end thereof to a second spaced apart location to cause fluid flow into said hollow cannula;
  (ii) an adapter assembly telescopically movable within said internal chamber of said housing of said syringe assembly from a first extended position to a second container assembly encapsulation position, said adapter assembly comprising:
    a. a hollow housing having a first open end for telescopically receiving a part of said body portion of said container of said container assembly and a second closed end;
    b. pusher means disposed within said hollow housing for moving said plunger of said container assembly as said adapter assembly moves from said first extended position to said second container assembly encapsulation position; and (c) locking means for locking said adapter assembly within said internal chamber of said syringe assembly, said locking means comprising a locking member provided on said housing of said syringe assembly and at least one locking tooth formed on said hollow housing of said adapter assembly for locking engagement with said locking member.

18. A syringe apparatus comprising:
(a) a syringe assembly including:
  (i) an elongated housing having side and end walls defining an internal chamber, said end wall having an opening therethrough; and
  (ii) cannula means including a hollow cannula disposed within said opening in said end wall for providing a fluid flow path to the exterior of the apparatus; and (b) a fluid containing assembly interconnected with said syringe assembly comprising:
  (i) a container assembly including:
    a. a container having a body portion, a fluid chamber, and first and second open ends;
    b. fluid flow control means disposed within said body portion of said container for controlling fluid flow from said fluid chamber toward said cannula means;
    c. closure means for sealably closing said first end of said container, said closure means being pierceable by said hollow cannula;
    d. a plunger telescopically movable within said container from a first location proximate said open end to a second spaced apart location to cause fluid flow into said hollow cannula; and
  (ii) an adapter assembly telescopically movable within said internal chamber of said housing of said syringe assembly from a first extended position to a second container assembly encapsulation position, said adapter assembly comprising:
  a. a hollow housing having walls defining an internal chamber having a first open end for telescopically receiving said container assembly and a second closed end; and
  b. a pusher rod connected to said second closed end of said hollow housing and extending into said hollow housing for moving said plunger of said container assembly as said adapter assembly moves from said first extended position to said second container assembly encapsulation position wherein said container is substantially encapsulated within said hollow housing.

19. An apparatus as defined in claim 18 further including a cover assembly comprising a cover having a first open end for telescopically receiving a part of said body portion of said container of said container assembly and a second end, said cover being removable from said container.

20. An apparatus as defined in claim 18 in which said fluid flow control means comprises:
  (a) a generally annular shaped plug disposed within said container; and
  (b) a stopper plug removably connected to said generally annular shaped plug.

21. An apparatus as defined in claim 18 in which said fluid flow control means comprises:
  (a) a generally cylindrically shaped pierceable plug disposed within said container for movement between first and second location; and
  (b) a cannula disposed within said container for piercing said pierceable plug upon movement thereof toward said second location.

22. An apparatus as defined in claim 18 in which said fluid flow control means comprises:
  (a) a fluid bypass chamber formed within said container; and
  (b) a generally cylindrically shaped elastomeric plug disposed within said container for movement between a first location spaced apart from said fluid bypass chamber to a second location within said fluid bypass chamber.

23. A syringe apparatus comprising:
(a) a syringe assembly including:
  (i) an elongated housing having side and end walls defining an internal chamber, said end wall having an opening therethrough; and
  (ii) cannula means including a hollow cannula disposed within said opening in said end wall for providing a fluid flow path to the exterior of the apparatus, said cannula means further comprising a threaded ring connectable with said container and being receivable within said opening in said end wall of said elongated housing of said syringe assembly, said hollow cannula being connected to said threaded ring; and
(b) a fluid containing assembly interconnected with said syringe assembly comprising:
  (i) a container assembly including:
    a. a container having a body portion, a fluid chamber, and first and second open ends;
    b. fluid flow control means disposed within said body portion of said container for controlling fluid flow from said fluid chamber toward said cannula means;
    c. closure means for sealably closing said first end of said container, said closure means being pierceable by said hollow cannula;
    d. a plunger telescopically movable within said container from a first location proximate said open end to a second spaced apart location to cause fluid flow into said hollow cannula; and
  (ii) an adapter assembly telescopically movable within said internal chamber of said housing of said syringe assembly from a first extended position to a second container assembly encapsulation position, said adapter assembly comprising:
    a. a hollow housing having a first open end for telescopically receiving a part of said body portion of said container of said container assembly and a second closed end; and
    b. a pusher rod connected to said second closed end of said hollow housing and extending into said hollow housing for moving said plunger of said container assembly as said adapter assembly moves from said first extended position to said second container assembly encapsulation position.

24. An apparatus as defined in claim 23 in which said hollow cannula comprises a piercing cannula having first and second ends.

25. An apparatus as defined in claim 23 in which said hollow cannula comprises a blunt end cannula.

26. A syringe apparatus comprising:
(a) a syringe assembly including an elongated housing having walls defining an internal chamber, one said wall having an opening therethrough;
(b) fluid delivery means for delivering fluid from said apparatus comprising cannula means, including a hollow cannula located proximate said opening in said wall of said syringe assembly for providing a fluid flow path to the exterior of the apparatus; and
(c) a fluid containing assembly operably associated with said syringe assembly and with said fluid delivery means, said fluid containing assembly comprising:
  (i) a container assembly including:
    a. a container having a fluid chamber, and first and second ends;
    b. fluid flow control means carried by said container for controlling fluid flow toward said cannula means;
    c. a plunger telescopically movable within said container from a first location to a second spaced apart location to cause fluid flow in a direction toward said hollow cannula; and
    d. adding means comprising a scaffold disposed within said container and a pharmaceutical removably connected to said scaffold; and
  (ii) an adapter assembly telescopically movable within said internal chamber of said housing of said syringe assembly from a first extended position to a second position, said adapter assembly comprising:
    a. a hollow housing having a first open end for telescopically receiving a part of said container of said of said container assembly and a second end;
    b. pusher means for moving said plunger of said container assembly as said adapter assembly moves from said first extended position to said second position; and
    c. a cover assembly removably connected to said fluid containing assembly including a cover receivable over said container of said container assembly.

27. An apparatus as defined in claim 26 in which said container of said container assembly comprises a plastic vial.

28. An apparatus as defined in claim 26 in which said elongated housing of said syringe assembly includes a generally cylindrical extension extending from said end wall and in which said cannula means comprises a pierceable cannula disposed within said cylindrical extension.

29. An apparatus as defined in claim 26 in which said elongated housing of said syringe assembly includes a generally cylindrical extension extending from said end wall and in which said cannula means comprises a pierceable cannula disposed within said cylindrical extension and a blunt end cannula extending outwardly from said cylindrical extension.

30. A syringe apparatus comprising:
    (a) a syringe assembly including:
        (i) an elongated housing having side and end walls defining an internal chamber, said end wall having an opening; and
        (ii) a hollow cannula disposed within said opening in said elongated housing and extending into said internal chamber thereof, said hollow cannula defining a fluid outlet passageway; and
    (b) a fluid containing assembly operably interconnectable with said syringe assembly comprising:
        (i) a container assembly including:
            a. a container having a body portion, a fluid chamber, and first and second ends, said body portion having a scaffold disposed therewithin and a beneficial agent removably connected to said scaffold;
            b. closure means for sealably closing one end of said container; and
            c. a plunger telescopically movable within said container from a first location proximate one end thereof to a second spaced apart location to cause fluid flow into said hollow cannula; and
        (ii) an adapter assembly telescopically movable within said internal chamber of said housing of said syringe assembly from a first extended position to a second container assembly encapsulation position, said adapter assembly comprising:
            a. a hollow housing having a first open end for telescopically receiving a part of said body portion of said container of said container assembly and a second closed end; and
            b. pusher means disposed within said hollow housing for moving said plunger of said container assembly as said adapter assembly moves from said first extended position to said second container assembly encapsulation position.

31. An apparatus as defined in claim 30 further including locking means for locking said adapter assembly within said internal chamber of said syringe assembly.

32. An apparatus as defined in claim 11 in which said container of said container assembly comprises a glass vial.

33. An apparatus as defined in claim 13 in which said closure means comprises a pierceable septum and in which said container assembly further includes a clamping ring for crimping engagement with said glass vial to hold said septum in position.

34. An apparatus as defined in claim 14 in which said hollow cannula of said syringe assembly comprises a hollow needle having a pierceable extremity for piercing said pierceable septum.

35. An apparatus as defined in claim 14 further including means for closing said fluid outlet passageway of said hollow cannula.

36. An apparatus as defined in claim 14 in which said hollow cannula of said syringe assembly comprises a hollow, blunt end cannula.

37. A syringe apparatus comprising:
    (a) a syringe assembly including an elongated housing having side and end walls defining an internal chamber, said end wall having an opening therethrough;
    (b) fluid delivery means for delivering fluid from said apparatus including a hollow cannula located proximate said opening in said end wall for providing a fluid flow path to the exterior of the apparatus; and
    (c) a fluid containing assembly operably associated with said syringe assembly and with said fluid delivery means, said fluid containing assembly comprising:
        (i) a container assembly including:
            a. a container having a body portion, including a first fluid containing chamber, a second fluid containing chamber, a third intermediate chamber and first and second ends;
            b. fluid flow control means carried by said container for controlling fluid flow in as direction toward said fluid delivery means, said fluid flow control means comprising fluid expelling means for expelling fluid from said second fluid containing chamber; and
            c. a first plunger telescopically movable within said first fluid containing chamber of said container from a first location proximate said first end of said container to a second spaced apart location to cause fluid flow in a direction toward said third intermediate chamber; and
        (ii) an adapter assembly telescopically movable within said internal chamber of said housing of said syringe assembly from a first extended position to a second advanced position, said adapter assembly comprising:
            a. a hollow housing having a first open end for telescopically receiving a part of said container of said container assembly and a second closed end; and
            b. pusher means for moving said plunger of said container assembly as said adapter assembly moves from said first extended position to said second position.

38. An apparatus as defined in claim 37 further including a second plunger movable within said second fluid containing chamber from a first location to a second location.

39. An apparatus as defined in claim 36 in which said flow control means comprises:
    (a) a fluid bypass chamber formed in said third intermediate chamber of said container, said fluid bypass chamber having at least one rib defining at least one fluid bypass channel; and
    (b) a plug receivable within said fluid bypass chamber.

40. An apparatus as defined in claim 37 in which said container assembly further includes quick coupling receiver means for allowing quick interconnection of said fluid delivery means with said container assembly.

41. An apparatus as defined in claim 40 in which said fluid delivery means comprises a coupler interconnectable with said quick coupling receiver means.

42. An apparatus as defined in claim 41 in which said flow control means further comprises check valve means carried by said quick coupling receiver means for controlling fluid flow from said second fluid containing chamber in a direction toward said fluid delivery means.

43. An apparatus as defined in claim 42 in which said check valve means comprises a check valve member having a body portion and an enlarged diameter portion and being movable from a first position to a second position.

44. An apparatus as defined in claim 43 in which said check valve member is movable from said first position to said second position by said coupler of said fluid delivery means.

45. An apparatus as defined in claim 37 in which said fluid expelling means comprises a fluid-expandable material.

46. A syringe apparatus comprising:
(a) a syringe assembly including an elongated housing having walls defining an internal chamber, one said wall having an opening therethrough;
(b) fluid delivery means for delivering fluid from said apparatus comprising cannula means, including a hollow cannula located proximate said opening in said wall of said syringe assembly for providing a fluid flow path to the exterior of the apparatus; and
(c) a fluid containing assembly operably associated with said syringe assembly and with said fluid delivery means, said fluid containing assembly comprising:
(i) a container assembly including:
   a. a container having a fluid chamber, and first and second ends;
   b. fluid flow control means carried by said container for controlling fluid flow toward said cannula means;
   c. a plunger telescopically movable within said container from a first location to a second spaced apart location to cause fluid flow in a direction toward said hollow cannula;
(ii) an adapter assembly telescopically movable within said internal chamber of said housing of said syringe assembly from a first extended position to a second position, said adapter assembly comprising:
   a. a hollow housing having a first open end for telescopically receiving a part of said container of said container assembly and a second end;
   b. pusher means for moving said plunger of said container assembly as said adapter assembly moves from said first extended position to said second position;
   c. a cover assembly removably connected to said fluid containing assembly including a cover receivable over said container of said container assembly; and
(iii) means for sealably interconnecting said cover with said adapter assembly.

47. An apparatus as defined in claim 46 in which said means for sealably interconnecting said cover with said adapter assembly comprises a label.

48. An apparatus as defined in claim 47 in which said cover of said cover assembly includes a first spiral wound, frangible portion and a second cylindrical portion, said first spiral wound, frangible portion being separable from said second cylindrical portion by tearing said label.

49. An apparatus as defined in claim 48 in which said flow control means comprises:
(a) a fluid bypass chamber formed in said container, said fluid bypass chamber having a plurality of circumferentially spaced ribs defining fluid bypass channels; and
(b) a plug receivable within said fluid bypass chamber.

50. An apparatus as defined in claim 49 in which said bypass chamber of said container includes spline-like plug stops for engagement by said plug receivable within said fluid bypass chamber.

* * * * *